United States Patent
LeBoeuf et al.

(10) Patent No.: US 11,337,655 B2
(45) Date of Patent: May 24, 2022

(54) PHYSIOLOGICAL MONITORING DEVICES AND METHODS USING OPTICAL SENSORS

(71) Applicant: Valencell, Inc., Raleigh, NC (US)

(72) Inventors: Steven Francis LeBoeuf, Raleigh, NC (US); Jesse Berkley Tucker, Youngsville, NC (US); Michael Edward Aumer, Raleigh, NC (US); Steven Matthew Just, Cary, NC (US); Mark Andrew Felice, Cary, NC (US)

(73) Assignee: Valencell, Inc., Raleigh, NC (US)

( * ) Notice: Subject to any disclaimer, the term of this patent is extended or adjusted under 35 U.S.C. 154(b) by 246 days.

(21) Appl. No.: 16/526,700

(22) Filed: Jul. 30, 2019

(65) Prior Publication Data

US 2019/0350532 A1  Nov. 21, 2019

Related U.S. Application Data

(63) Continuation of application No. 16/503,191, filed on Jul. 3, 2019, now Pat. No. 11,185,290, which is a
(Continued)

(51) Int. Cl.
*A61B 5/1455* (2006.01)
*A61B 5/00* (2006.01)
(Continued)

(52) U.S. Cl.
CPC .......... *A61B 5/7203* (2013.01); *A61B 5/0059* (2013.01); *A61B 5/01* (2013.01);
(Continued)

(58) Field of Classification Search
CPC ... A61B 5/7203; A61B 5/7271; A61B 5/1455; A61B 5/68; A61B 5/02055;
(Continued)

(56) References Cited

U.S. PATENT DOCUMENTS 3,595,219 A  7/1971 Friedlander et al.
4,240,882 A  12/1980 Ang et al.
(Continued)

FOREIGN PATENT DOCUMENTS

CN  101212927 A  7/2008
CN  201438747 U  4/2010
(Continued)

OTHER PUBLICATIONS

"Communication with European Search Report", EP Application No. 20185366.0, dated Oct. 1, 2020.
(Continued)

*Primary Examiner* — Chu Chuan Liu
(74) *Attorney, Agent, or Firm* — Myers Bigel, P.A.

(57) ABSTRACT

A monitoring device configured to be attached to a subject includes a photoplethysmography (PPG) sensor configured to measure physiological information from the subject, and at least one processor configured to process signals from the PPG sensor to determine heart rate and RR-interval (RRi) for the subject, and to determine a heart rate pattern for the subject over a period of time. The at least one processor is configured to change a sampling frequency of the PPG sensor for determining RRi in response to the determined heart rate pattern. The at least one processor is configured to reduce the sampling frequency of the PPG sensor in response to determining a pattern of heart rate below a threshold.

24 Claims, 15 Drawing Sheets

Related U.S. Application Data continuation of application No. 14/807,149, filed on Jul. 23, 2015, now abandoned.

(60) Provisional application No. 62/109,196, filed on Jan. 29, 2015, provisional application No. 62/030,951, filed on Jul. 30, 2014.

(51) Int. Cl.

| | | |
|---|---|---|
| *A61B 5/0205* | (2006.01) | |
| *A61B 5/024* | (2006.01) | |
| *A61B 5/021* | (2006.01) | |
| *A61B 5/01* | (2006.01) | |
| *A61B 5/11* | (2006.01) | |
| *A61B 5/16* | (2006.01) | |
| *G05B 19/048* | (2006.01) | |
| *A61B 5/08* | (2006.01) | |

(52) U.S. Cl.
CPC ............ *A61B 5/021* (2013.01); *A61B 5/0205* (2013.01); *A61B 5/02055* (2013.01); *A61B 5/02416* (2013.01); *A61B 5/02427* (2013.01); *A61B 5/1118* (2013.01); *A61B 5/1123* (2013.01); *A61B 5/14551* (2013.01); *A61B 5/14552* (2013.01); *A61B 5/165* (2013.01); *A61B 5/4266* (2013.01); *A61B 5/443* (2013.01); *A61B 5/4809* (2013.01); *A61B 5/68* (2013.01); *A61B 5/6803* (2013.01); *A61B 5/6815* (2013.01); *A61B 5/6816* (2013.01); *A61B 5/6826* (2013.01); *A61B 5/72* (2013.01); *A61B 5/7207* (2013.01); *A61B 5/7271* (2013.01); *A61B 5/7282* (2013.01); *A61B 5/742* (2013.01); *G05B 19/048* (2013.01); *A61B 5/024* (2013.01); *A61B 5/02405* (2013.01); *A61B 5/0816* (2013.01); *A61B 5/6831* (2013.01); *A61B 2503/10* (2013.01); *A61B 2560/0242* (2013.01); *A61B 2560/0247* (2013.01); *A61B 2560/0266* (2013.01); *G05B 2219/2652* (2013.01)

(58) Field of Classification Search
CPC ..... A61B 5/0059; A61B 5/165; A61B 5/6815; A61B 5/6816; A61B 5/02427; A61B 5/72; A61B 5/02416; A61B 5/742; A61B 5/021; A61B 5/7207; A61B 5/4266; A61B 5/01; A61B 5/443; A61B 5/4809; A61B 5/1118; A61B 5/0205; A61B 5/1123; A61B 5/14551; A61B 5/14552; A61B 5/6803; A61B 5/6826; A61B 5/024; A61B 5/02405; A61B 5/0816
See application file for complete search history.

(56) References Cited

U.S. PATENT DOCUMENTS

| | | |
|---|---|---|
| 4,331,154 A | 5/1982 | Broadwater et al. |
| 4,438,772 A | 3/1984 | Slavin |
| 4,491,760 A | 1/1985 | Linvill |
| 4,521,499 A | 6/1985 | Switzer |
| 4,541,905 A | 9/1985 | Kuwana et al. |
| 4,592,807 A | 6/1986 | Switzer |
| 4,655,225 A | 4/1987 | Dahne et al. |
| 4,830,014 A | 5/1989 | Goodman et al. |
| 4,882,492 A | 11/1989 | Schlager |
| 4,896,676 A | 1/1990 | Sasaki |
| 4,928,704 A | 5/1990 | Hardt |
| 4,957,109 A | 9/1990 | Groeger et al. |
| 5,002,060 A | 3/1991 | Nedivi |
| 5,007,423 A | 4/1991 | Branstetter et al. |
| 5,022,970 A | 6/1991 | Cook et al. |
| 5,025,791 A | 6/1991 | Niwa |
| 5,079,421 A | 1/1992 | Knudson et al. |
| 5,080,098 A | 1/1992 | Willett et al. |
| 5,086,229 A | 2/1992 | Rosenthal et al. |
| 5,143,078 A | 9/1992 | Mather et al. |
| 5,226,417 A | 7/1993 | Swedlow et al. |
| 5,237,994 A | 8/1993 | Goldberger |
| 5,348,002 A | 9/1994 | Caro |
| 5,377,100 A | 12/1994 | Pope et al. |
| 5,482,036 A | 1/1996 | Diab et al. |
| 5,492,129 A | 2/1996 | Greenberger |
| 5,499,301 A | 3/1996 | Sudo et al. |
| 5,581,648 A | 12/1996 | Sahagen |
| 5,596,987 A | 1/1997 | Chance |
| 5,662,117 A | 9/1997 | Bittman |
| 5,673,692 A | 10/1997 | Schulze et al. |
| 5,697,374 A | 12/1997 | Odagiri et al. |
| 5,711,308 A | 1/1998 | Singer |
| 5,725,480 A | 3/1998 | Oosta et al. |
| 5,743,260 A | 4/1998 | Chung et al. |
| 5,779,631 A | 7/1998 | Chance |
| 5,797,841 A | 8/1998 | Delonzor et al. |
| 5,807,114 A | 9/1998 | Hodges et al. |
| 5,807,267 A | 9/1998 | Bryars et al. |
| 5,853,005 A | 12/1998 | Scanlon |
| 5,904,654 A | 5/1999 | Wohltmann et al. |
| 5,906,582 A | 5/1999 | Kondo et al. |
| 5,938,593 A | 8/1999 | Quellette |
| 5,964,701 A | 10/1999 | Asada et al. |
| 5,971,931 A | 10/1999 | Raff |
| 5,974,338 A | 10/1999 | Asano et al. |
| 5,995,858 A | 11/1999 | Kinast |
| 6,004,274 A | 12/1999 | Nolan et al. |
| 6,013,007 A | 1/2000 | Root et al. |
| 6,023,541 A | 2/2000 | Merchant et al. |
| 6,030,342 A | 2/2000 | Amano et al. |
| 6,045,511 A | 4/2000 | Ott et al. |
| 6,067,006 A | 5/2000 | O'Brien |
| 6,070,093 A | 5/2000 | Oosta et al. |
| 6,078,829 A | 6/2000 | Uchida et al. |
| 6,080,110 A | 6/2000 | Thorgersen |
| 6,081,742 A | 6/2000 | Amano et al. |
| 6,088,607 A * | 7/2000 | Diab ................. A61B 5/02427 600/322 |
| 6,186,145 B1 | 2/2001 | Brown |
| 6,198,394 B1 | 3/2001 | Jacobsen et al. |
| 6,198,951 B1 | 3/2001 | Kosuda et al. |
| 6,205,354 B1 | 3/2001 | Gellermann et al. |
| 6,231,519 B1 | 5/2001 | Blants et al. |
| 6,283,915 B1 | 9/2001 | Aceti et al. |
| 6,285,816 B1 | 9/2001 | Anderson et al. |
| 6,289,230 B1 | 9/2001 | Chaiken et al. |
| 6,298,314 B1 | 10/2001 | Blackadar et al. |
| 6,332,868 B1 | 12/2001 | Sato et al. |
| 6,358,216 B1 | 3/2002 | Kraus et al. |
| 6,361,660 B1 | 3/2002 | Goldstein |
| 6,371,925 B1 | 4/2002 | Imai et al. |
| 6,374,129 B1 | 4/2002 | Chin et al. |
| 6,402,690 B1 | 6/2002 | Rhee et al. |
| 6,415,167 B1 | 7/2002 | Blank et al. |
| 6,443,890 B1 | 9/2002 | Schulze et al. |
| 6,444,474 B1 | 9/2002 | Thomas et al. |
| 6,454,718 B1 | 9/2002 | Clift |
| 6,458,080 B1 | 10/2002 | Brown et al. |
| 6,470,893 B1 | 10/2002 | Boesen |
| 6,513,532 B2 | 2/2003 | Mault et al. |
| 6,514,278 B1 | 2/2003 | Hibst et al. |
| 6,527,711 B1 | 3/2003 | Stivoric et al. |
| 6,527,712 B1 | 3/2003 | Brown et al. |
| 6,529,754 B2 | 3/2003 | Kondo |
| 6,534,012 B1 | 3/2003 | Hazen et al. |
| 6,556,852 B1 | 4/2003 | Schulze et al. |
| 6,569,094 B2 | 5/2003 | Suzuki et al. |
| 6,571,117 B1 | 5/2003 | Marbach |
| 6,605,038 B1 | 8/2003 | Teller et al. |
| 6,616,613 B1 | 9/2003 | Goodman |
| 6,631,196 B1 | 10/2003 | Taenzer et al. |
| 6,647,378 B2 | 11/2003 | Kindo |

(56) References Cited

U.S. PATENT DOCUMENTS

| | | |
|---|---|---|
| 6,656,116 B2 | 12/2003 | Kim et al. |
| 6,694,180 B1 | 2/2004 | Boesen |
| 6,745,061 B1 | 6/2004 | Hicks et al. |
| 6,748,254 B2 | 6/2004 | O'Neil et al. |
| 6,760,610 B2 | 7/2004 | Tschupp et al. |
| 6,783,501 B2 | 8/2004 | Takahashi et al. |
| 6,808,473 B2 | 10/2004 | Hisano et al. |
| 6,859,658 B1 | 2/2005 | Krug |
| 6,893,396 B2 | 5/2005 | Schulze et al. |
| 6,941,239 B2 | 9/2005 | Unuma et al. |
| 6,953,435 B2 | 10/2005 | Kondo et al. |
| 6,996,427 B2 | 2/2006 | Ali et al. |
| 6,997,879 B1 | 2/2006 | Turcott |
| 7,018,338 B2 | 3/2006 | Vetter et al. |
| 7,024,369 B1 | 4/2006 | Brown et al. |
| 7,030,359 B2 | 4/2006 | Römhild |
| 7,034,694 B2 | 4/2006 | Yamaguchi et al. |
| 7,041,062 B2 | 5/2006 | Friedrichs et al. |
| 7,043,287 B1 | 5/2006 | Khalil et al. |
| 7,054,674 B2 | 5/2006 | Cane et al. |
| 7,088,234 B2 | 8/2006 | Naito et al. |
| 7,107,088 B2 | 9/2006 | Aceti |
| 7,113,815 B2 | 9/2006 | O'Neil et al. |
| 7,117,032 B2 | 10/2006 | Childre et al. |
| 7,163,512 B1 | 1/2007 | Childre et al. |
| 7,175,601 B2 | 2/2007 | Verjus et al. |
| 7,209,775 B2 | 4/2007 | Bae et al. |
| 7,217,224 B2 | 5/2007 | Thomas |
| 7,252,639 B2 | 8/2007 | Kimura et al. |
| 7,263,396 B2 | 8/2007 | Chen et al. |
| 7,289,837 B2 | 10/2007 | Mannheimer et al. |
| 7,295,866 B2 * | 11/2007 | Al-Ali ............... A61B 5/14551 600/323 |
| 7,336,982 B2 | 2/2008 | Yoo et al. |
| 7,341,559 B2 | 3/2008 | Schultz et al. |
| 7,376,451 B2 | 5/2008 | Mahony et al. |
| 7,470,234 B1 | 12/2008 | Elhag et al. |
| 7,483,730 B2 | 1/2009 | Diab et al. |
| 7,486,988 B2 | 2/2009 | Goodall et al. |
| 7,507,207 B2 | 3/2009 | Sakai et al. |
| 7,519,327 B2 | 4/2009 | White |
| 7,526,327 B2 | 4/2009 | Blondeau et al. |
| 7,583,994 B2 | 9/2009 | Scholz |
| 7,625,285 B2 | 12/2009 | Breving |
| 7,652,569 B2 | 1/2010 | Kiff et al. |
| 7,689,437 B1 | 3/2010 | Teller et al. |
| 7,695,440 B2 | 4/2010 | Kondo et al. |
| 7,725,147 B2 | 5/2010 | Li et al. |
| 7,756,559 B2 | 7/2010 | Abreu |
| 7,843,325 B2 | 11/2010 | Otto |
| 7,894,869 B2 | 2/2011 | Hoarau |
| 7,914,468 B2 | 3/2011 | Shalon et al. |
| 7,991,448 B2 | 8/2011 | Edgar et al. |
| 7,998,079 B2 | 8/2011 | Nagai et al. |
| 8,050,728 B2 | 11/2011 | Al-Ali et al. |
| 8,055,319 B2 | 11/2011 | Oh et al. |
| 8,055,330 B2 | 11/2011 | Egozi |
| 8,059,924 B1 | 11/2011 | Letant et al. |
| 8,130,105 B2 | 3/2012 | Al-Ali et al. |
| 8,137,270 B2 | 3/2012 | Keenan et al. |
| 8,157,730 B2 | 4/2012 | LeBoeuf et al. |
| 8,172,459 B2 | 5/2012 | Abreu |
| 8,175,670 B2 | 5/2012 | Baker, Jr. et al. |
| 8,204,730 B2 | 6/2012 | Liu et al. |
| 8,204,786 B2 | 6/2012 | LeBoeuf et al. |
| 8,233,955 B2 | 7/2012 | Al-Ali et al. |
| 8,251,903 B2 | 8/2012 | LeBoeuf et al. |
| 8,255,027 B2 | 8/2012 | Al-Ali et al. |
| 8,255,029 B2 | 8/2012 | Addison et al. |
| 8,303,512 B2 | 11/2012 | Kosuda et al. |
| 8,320,982 B2 | 11/2012 | LeBoeuf et al. |
| 8,323,982 B2 | 12/2012 | LeBoeuf et al. |
| 8,328,420 B2 | 12/2012 | Abreu |
| 8,416,959 B2 | 4/2013 | Lott et al. |
| 8,430,817 B1 * | 4/2013 | Al-Ali ............... A61B 5/742 600/301 |
| 8,491,492 B2 | 7/2013 | Shinar et al. |
| 8,504,679 B2 | 8/2013 | Spire et al. |
| 8,506,524 B2 | 8/2013 | Graskov et al. |
| 8,512,242 B2 | 8/2013 | LeBoeuf et al. |
| 8,647,270 B2 | 2/2014 | LeBoeuf et al. |
| 8,652,040 B2 | 2/2014 | LeBoeuf et al. |
| 8,652,409 B2 | 2/2014 | LeBoeuf et al. |
| 8,679,008 B2 | 3/2014 | Hughes et al. |
| 8,700,111 B2 | 4/2014 | LeBoeuf et al. |
| 8,702,607 B2 | 4/2014 | LeBoeuf et al. |
| 8,730,048 B2 | 5/2014 | Shen et al. |
| 8,788,002 B2 | 7/2014 | LeBoeuf et al. |
| 8,886,269 B2 | 11/2014 | LeBoeuf et al. |
| 8,888,701 B2 | 11/2014 | LeBoeuf et al. |
| 8,923,941 B2 | 12/2014 | LeBoeuf et al. |
| 8,929,965 B2 | 1/2015 | LeBoeuf et al. |
| 8,929,966 B2 | 1/2015 | LeBoeuf et al. |
| 8,934,952 B2 | 1/2015 | LeBoeuf et al. |
| 8,942,776 B2 | 1/2015 | LeBoeuf et al. |
| 8,961,415 B2 | 2/2015 | LeBoeuf et al. |
| 9,005,129 B2 | 4/2015 | Venkatraman et al. |
| 9,649,055 B2 | 5/2017 | Ashe et al. |
| 10,524,736 B2 | 1/2020 | Gross |
| 2001/0049471 A1 | 12/2001 | Suzuki et al. |
| 2002/0035340 A1 | 3/2002 | Fraden et al. |
| 2002/0143242 A1 | 10/2002 | Nemirovski |
| 2002/0156386 A1 | 10/2002 | Dardik et al. |
| 2002/0156654 A1 | 10/2002 | Roe et al. |
| 2002/0186137 A1 | 12/2002 | Skardon |
| 2002/0188210 A1 | 12/2002 | Aizawa |
| 2002/0194002 A1 | 12/2002 | Petrushin |
| 2003/0002705 A1 | 1/2003 | Boesen |
| 2003/0007631 A1 | 1/2003 | Bolognesi et al. |
| 2003/0045785 A1 | 3/2003 | Diab et al. |
| 2003/0050563 A1 | 3/2003 | Suribhotla et al. |
| 2003/0064712 A1 | 4/2003 | Gaston et al. |
| 2003/0065257 A1 | 4/2003 | Mault et al. |
| 2003/0083583 A1 | 5/2003 | Kovtun et al. |
| 2003/0109030 A1 | 6/2003 | Uchida et al. |
| 2003/0181795 A1 | 9/2003 | Suzuki et al. |
| 2003/0212336 A1 | 11/2003 | Lee et al. |
| 2003/0220584 A1 | 11/2003 | Honeyager et al. |
| 2003/0222268 A1 | 12/2003 | Yocom et al. |
| 2004/0004547 A1 | 1/2004 | Appelt et al. |
| 2004/0022700 A1 | 2/2004 | Kim et al. |
| 2004/0030581 A1 | 2/2004 | Leven |
| 2004/0034289 A1 | 2/2004 | Teller et al. |
| 2004/0034293 A1 | 2/2004 | Kimball |
| 2004/0054291 A1 | 3/2004 | Schulz et al. |
| 2004/0075677 A1 | 4/2004 | Loyall et al. |
| 2004/0077934 A1 | 4/2004 | Massad |
| 2004/0082842 A1 | 4/2004 | Lumba et al. |
| 2004/0103146 A1 | 5/2004 | Park |
| 2004/0117204 A1 | 6/2004 | Mazar et al. |
| 2004/0120844 A1 | 6/2004 | Tribelsky et al. |
| 2004/0122294 A1 | 6/2004 | Hatlestad et al. |
| 2004/0122702 A1 | 6/2004 | Sabol et al. |
| 2004/0133123 A1 | 7/2004 | Leonhardt et al. |
| 2004/0135571 A1 | 7/2004 | Uutela et al. |
| 2004/0138578 A1 | 7/2004 | Pineda et al. |
| 2004/0186390 A1 | 9/2004 | Ross et al. |
| 2004/0219056 A1 | 11/2004 | Tribelsky et al. |
| 2004/0220488 A1 | 11/2004 | Vyshedskiy et al. |
| 2004/0225207 A1 | 11/2004 | Bae et al. |
| 2004/0228494 A1 | 11/2004 | Smith |
| 2004/0242976 A1 | 12/2004 | Abreu |
| 2005/0004458 A1 | 1/2005 | Kanayama et al. |
| 2005/0027216 A1 | 2/2005 | Guillemaud et al. |
| 2005/0030540 A1 | 2/2005 | Thornton |
| 2005/0033200 A1 | 2/2005 | Soehren et al. |
| 2005/0038349 A1 | 2/2005 | Choi et al. |
| 2005/0043600 A1 | 2/2005 | Diab et al. |
| 2005/0043630 A1 | 2/2005 | Buchert et al. |
| 2005/0054908 A1 | 3/2005 | Blank et al. |
| 2005/0058456 A1 | 3/2005 | Yoo |
| 2005/0059870 A1 | 3/2005 | Aceti |
| 2005/0084666 A1 | 4/2005 | Pong et al. |

(56) References Cited

U.S. PATENT DOCUMENTS

| | | |
|---|---|---|
| 2005/0101845 A1 | 5/2005 | Nihtila |
| 2005/0101872 A1 | 5/2005 | Sattler et al. |
| 2005/0113167 A1 | 5/2005 | Buchner et al. |
| 2005/0113656 A1 | 5/2005 | Chance |
| 2005/0113703 A1 | 5/2005 | Farringdon et al. |
| 2005/0116820 A1 | 6/2005 | Goldreich |
| 2005/0119833 A1 | 6/2005 | Nanikashvili |
| 2005/0148883 A1 | 7/2005 | Boesen |
| 2005/0154264 A1 | 7/2005 | Lecompte et al. |
| 2005/0177034 A1 | 8/2005 | Beaumont |
| 2005/0187448 A1 | 8/2005 | Petersen et al. |
| 2005/0187453 A1 | 8/2005 | Petersen et al. |
| 2005/0192515 A1 | 9/2005 | Givens et al. |
| 2005/0196009 A1 | 9/2005 | Boesen |
| 2005/0203349 A1 | 9/2005 | Nanikashvili |
| 2005/0203357 A1 | 9/2005 | Debreczeny et al. |
| 2005/0209516 A1 | 9/2005 | Fraden |
| 2005/0222487 A1 | 10/2005 | Miller et al. |
| 2005/0222903 A1 | 10/2005 | Buchheit et al. |
| 2005/0228244 A1 | 10/2005 | Banet |
| 2005/0228299 A1 | 10/2005 | Banet |
| 2005/0240087 A1 | 10/2005 | Keenan et al. |
| 2005/0258816 A1 | 11/2005 | Zen et al. |
| 2005/0259811 A1 | 11/2005 | Kimm et al. |
| 2006/0009685 A1 | 1/2006 | Finarov et al. |
| 2006/0012567 A1 | 1/2006 | Sicklinger |
| 2006/0063993 A1 | 3/2006 | Yu et al. |
| 2006/0064037 A1 | 3/2006 | Shalon et al. |
| 2006/0084878 A1 | 4/2006 | Banet et al. |
| 2006/0084879 A1 | 4/2006 | Nazarian et al. |
| 2006/0122520 A1 | 6/2006 | Banet et al. |
| 2006/0123885 A1 | 6/2006 | Yates et al. |
| 2006/0140425 A1 | 6/2006 | Berg et al. |
| 2006/0142665 A1 | 6/2006 | Garay et al. |
| 2006/0202816 A1 | 9/2006 | Crump et al. |
| 2006/0205083 A1 | 9/2006 | Zhao |
| 2006/0210058 A1 | 9/2006 | Kock et al. |
| 2006/0211922 A1 | 9/2006 | Al-Ali et al. |
| 2006/0211924 A1 | 9/2006 | Dalke et al. |
| 2006/0217598 A1 | 9/2006 | Miyajima et al. |
| 2006/0217615 A1 | 9/2006 | Huiku et al. |
| 2006/0224059 A1 | 10/2006 | Swedlow et al. |
| 2006/0240558 A1 | 10/2006 | Zhao |
| 2006/0246342 A1 | 11/2006 | MacPhee |
| 2006/0251277 A1 | 11/2006 | Cho |
| 2006/0251334 A1 | 11/2006 | Oba et al. |
| 2006/0252999 A1 | 11/2006 | Devaul et al. |
| 2006/0264730 A1 | 11/2006 | Stivoric et al. |
| 2006/0292533 A1 | 12/2006 | Selod |
| 2006/0293921 A1 | 12/2006 | McCarthy et al. |
| 2007/0004449 A1 | 1/2007 | Sham |
| 2007/0004969 A1 | 1/2007 | Kong et al. |
| 2007/0015992 A1 | 1/2007 | Filkins et al. |
| 2007/0021206 A1 | 1/2007 | Sunnen |
| 2007/0027367 A1 | 2/2007 | Oliver et al. |
| 2007/0027399 A1 | 2/2007 | Chou |
| 2007/0036383 A1 | 2/2007 | Romero |
| 2007/0050215 A1 | 3/2007 | Kil et al. |
| 2007/0060800 A1 | 3/2007 | Drinan et al. |
| 2007/0063850 A1 | 3/2007 | Devaul et al. |
| 2007/0082789 A1 | 4/2007 | Nissila et al. |
| 2007/0083092 A1 | 4/2007 | Rippo et al. |
| 2007/0083095 A1 | 4/2007 | Rippo et al. |
| 2007/0088221 A1 | 4/2007 | Stahmann |
| 2007/0093702 A1 | 4/2007 | Yu et al. |
| 2007/0106167 A1 | 5/2007 | Kinast |
| 2007/0112273 A1 | 5/2007 | Rogers |
| 2007/0112598 A1 | 5/2007 | Heckerman et al. |
| 2007/0116314 A1 | 5/2007 | Grilliot et al. |
| 2007/0118043 A1 | 5/2007 | Oliver et al. |
| 2007/0165872 A1 | 7/2007 | Bridger et al. |
| 2007/0167850 A1 | 7/2007 | Russell et al. |
| 2007/0191718 A1 | 8/2007 | Nakamura |
| 2007/0197878 A1 | 8/2007 | Shklarski |
| 2007/0197881 A1 | 8/2007 | Wolf et al. |
| 2007/0213020 A1 | 9/2007 | Novac |
| 2007/0230714 A1 | 10/2007 | Armstrong |
| 2007/0233403 A1 | 10/2007 | Alwan et al. |
| 2007/0265097 A1 | 11/2007 | Havukainen |
| 2007/0270667 A1 | 11/2007 | Coppi et al. |
| 2007/0270671 A1 | 11/2007 | Gal |
| 2007/0293781 A1 | 12/2007 | Sims et al. |
| 2007/0299330 A1 | 12/2007 | Couronne et al. |
| 2008/0004536 A1 | 1/2008 | Baxi et al. |
| 2008/0015424 A1 | 1/2008 | Bernreuter |
| 2008/0039731 A1 | 2/2008 | McCombie et al. |
| 2008/0076972 A1 | 3/2008 | Dorogusker et al. |
| 2008/0081963 A1 | 4/2008 | Naghavi et al. |
| 2008/0086533 A1 | 4/2008 | Neuhauser et al. |
| 2008/0096726 A1 | 4/2008 | Riley et al. |
| 2008/0114220 A1 | 5/2008 | Banet et al. |
| 2008/0132798 A1 | 6/2008 | Hong et al. |
| 2008/0141301 A1 | 6/2008 | Azzaro et al. |
| 2008/0154098 A1 | 6/2008 | Morris et al. |
| 2008/0154105 A1 | 6/2008 | Lemay |
| 2008/0165017 A1 | 7/2008 | Schwartz |
| 2008/0170600 A1 | 7/2008 | Sattler et al. |
| 2008/0171945 A1 | 7/2008 | Dotter |
| 2008/0177162 A1 | 7/2008 | Bae et al. |
| 2008/0200774 A1 | 8/2008 | Luo |
| 2008/0200775 A1 | 8/2008 | Lynn |
| 2008/0203144 A1 | 8/2008 | Kim |
| 2008/0221461 A1 | 9/2008 | Zhou et al. |
| 2008/0249594 A1 | 10/2008 | Dietrich |
| 2008/0269626 A1 | 10/2008 | Gallagher et al. |
| 2008/0287752 A1 | 11/2008 | Stroetz et al. |
| 2009/0005662 A1 | 1/2009 | Petersen et al. |
| 2009/0006457 A1 | 1/2009 | Stivoric et al. |
| 2009/0010461 A1 | 1/2009 | Klinghult et al. |
| 2009/0030350 A1 | 1/2009 | Yang et al. |
| 2009/0054751 A1 | 2/2009 | Babashan et al. |
| 2009/0054752 A1 | 2/2009 | Jonnalagadda et al. |
| 2009/0069645 A1 | 3/2009 | Nielsen et al. |
| 2009/0082994 A1 | 3/2009 | Schuler et al. |
| 2009/0088611 A1 | 4/2009 | Buschmann |
| 2009/0093687 A1 | 4/2009 | Telfort et al. |
| 2009/0105548 A1 | 4/2009 | Bart |
| 2009/0105556 A1 | 4/2009 | Fricke et al. |
| 2009/0131761 A1 | 5/2009 | Moroney III et al. |
| 2009/0131764 A1 | 5/2009 | Lee et al. |
| 2009/0175456 A1 | 7/2009 | Johnson |
| 2009/0177097 A1 | 7/2009 | Ma et al. |
| 2009/0214060 A1 | 8/2009 | Chuang et al. |
| 2009/0221888 A1 | 9/2009 | Wijesiriwardana |
| 2009/0227853 A1 | 9/2009 | Wijesiriwardana |
| 2009/0240125 A1 | 9/2009 | Such et al. |
| 2009/0253992 A1 | 10/2009 | Van Der Loo |
| 2009/0253996 A1 | 10/2009 | Lee et al. |
| 2009/0264711 A1 | 10/2009 | Schuler et al. |
| 2009/0270698 A1 | 10/2009 | Shioi et al. |
| 2009/0287067 A1 | 11/2009 | Dorogusker et al. |
| 2009/0299215 A1 | 12/2009 | Zhang |
| 2010/0004517 A1 | 1/2010 | Bryenton et al. |
| 2010/0022861 A1 | 1/2010 | Cinbis et al. |
| 2010/0045663 A1 | 2/2010 | Chen et al. |
| 2010/0100013 A1 | 4/2010 | Hu et al. |
| 2010/0113948 A1 | 5/2010 | Yang et al. |
| 2010/0168531 A1 | 7/2010 | Shaltis et al. |
| 2010/0172522 A1 | 7/2010 | Mooring et al. |
| 2010/0179389 A1 | 7/2010 | Moroney et al. |
| 2010/0185105 A1 | 7/2010 | Baldinger |
| 2010/0217100 A1 | 8/2010 | LeBoeuf |
| 2010/0217103 A1 | 8/2010 | Abdul-Hafiz et al. |
| 2010/0222655 A1 | 9/2010 | Starr et al. |
| 2010/0228315 A1 | 9/2010 | Nielsen |
| 2010/0234714 A1 | 9/2010 | Mercier et al. |
| 2010/0268056 A1 | 10/2010 | Picard et al. |
| 2010/0274100 A1 | 10/2010 | Behar et al. |
| 2010/0274109 A1 | 10/2010 | Hu et al. |
| 2010/0292589 A1 | 11/2010 | Goodman |
| 2010/0298653 A1 | 11/2010 | McCombie et al. |
| 2010/0324384 A1 | 12/2010 | Moon et al. |
| 2011/0028810 A1 | 2/2011 | Van Slyke et al. |
| 2011/0028813 A1 | 2/2011 | Watson et al. |

(56) References Cited

U.S. PATENT DOCUMENTS

| | | |
|---|---|---|
| 2011/0081037 A1 | 4/2011 | Oh et al. |
| 2011/0098112 A1 | 4/2011 | LeBoeuf |
| 2011/0105869 A1 | 5/2011 | Wilson et al. |
| 2011/0112382 A1 | 5/2011 | Li et al. |
| 2011/0130638 A1 | 6/2011 | Raridan, Jr. |
| 2011/0142371 A1 | 6/2011 | King et al. |
| 2011/0245637 A1 | 10/2011 | McKenna |
| 2011/0288379 A1 | 11/2011 | Wu |
| 2012/0030547 A1 | 2/2012 | Raptis et al. |
| 2012/0095303 A1 | 4/2012 | He |
| 2012/0156933 A1 | 6/2012 | Kreger et al. |
| 2012/0179011 A1 | 7/2012 | Moon et al. |
| 2012/0203081 A1 | 8/2012 | LeBoeuf et al. |
| 2012/0226111 A1 | 9/2012 | LeBoeuf et al. |
| 2012/0226112 A1 | 9/2012 | LeBoeuf et al. |
| 2012/0277548 A1 | 11/2012 | Burton |
| 2012/0283577 A1 | 11/2012 | LeBoeuf et al. |
| 2012/0296184 A1 | 11/2012 | LeBoeuf et al. |
| 2013/0053661 A1 | 2/2013 | Alberth et al. |
| 2013/0072765 A1 | 3/2013 | Kahn et al. |
| 2013/0173171 A1 | 7/2013 | Drysdale et al. |
| 2013/0217979 A1 | 8/2013 | Blackadar et al. |
| 2013/0245387 A1 | 9/2013 | Patel |
| 2013/0324856 A1 | 12/2013 | Lisogurski et al. |
| 2013/0336495 A1 | 12/2013 | Burgett et al. |
| 2014/0012105 A1 | 1/2014 | LeBoeuf et al. |
| 2014/0051940 A1 | 2/2014 | Messerschmidt |
| 2014/0051948 A1 | 2/2014 | LeBoeuf et al. |
| 2014/0052567 A1 | 2/2014 | Bhardwaj et al. |
| 2014/0058220 A1 | 2/2014 | LeBoeuf et al. |
| 2014/0073486 A1 | 3/2014 | Ahmed et al. |
| 2014/0094663 A1 | 4/2014 | LeBoeuf et al. |
| 2014/0100432 A1 | 4/2014 | Golda et al. |
| 2014/0114147 A1 | 4/2014 | Romesburg et al. |
| 2014/0127996 A1 | 5/2014 | Park et al. |
| 2014/0128690 A1 | 5/2014 | LeBoeuf et al. |
| 2014/0135596 A1 | 5/2014 | LeBoeuf et al. |
| 2014/0140567 A1 | 5/2014 | LeBoeuf et al. |
| 2014/0197946 A1 | 7/2014 | Park et al. |
| 2014/0206954 A1 | 7/2014 | Yuen et al. |
| 2014/0213912 A1 | 7/2014 | Su |
| 2014/0219467 A1 | 8/2014 | Kurtz |
| 2014/0235967 A1 | 8/2014 | LeBoeuf et al. |
| 2014/0235968 A1 | 8/2014 | LeBoeuf et al. |
| 2014/0236531 A1 | 8/2014 | Carter |
| 2014/0243617 A1 | 8/2014 | LeBoeuf et al. |
| 2014/0243620 A1 | 8/2014 | LeBoeuf et al. |
| 2014/0275852 A1 | 9/2014 | Hong et al. |
| 2014/0275855 A1 | 9/2014 | LeBoeuf et al. |
| 2014/0278139 A1 | 9/2014 | Hong et al. |
| 2014/0287833 A1 | 9/2014 | LeBoeuf et al. |
| 2014/0288396 A1 | 9/2014 | LeBoeuf et al. |
| 2014/0323829 A1 | 10/2014 | LeBoeuf et al. |
| 2014/0323830 A1 | 10/2014 | LeBoeuf et al. |
| 2014/0323880 A1 | 10/2014 | Ahmed et al. |
| 2014/0378844 A1 | 12/2014 | Fei |
| 2015/0031967 A1 | 1/2015 | LeBoeuf et al. |
| 2015/0032009 A1 | 1/2015 | LeBoeuf et al. |
| 2016/0278646 A1 | 9/2016 | Hu et al. |
| 2017/0251295 A1 | 8/2017 | Pergament et al. |

FOREIGN PATENT DOCUMENTS

| | | |
|---|---|---|
| DE | 3910749 A1 | 10/1990 |
| EP | 1 297 784 A1 | 4/2003 |
| EP | 1 480 278 A2 | 11/2004 |
| EP | 2 077 091 A2 | 7/2009 |
| EP | 2 182 839 B1 | 10/2011 |
| GB | 2 408 209 A | 5/2005 |
| GB | 2 411 719 A | 9/2005 |
| JP | 7-241279 | 9/1995 |
| JP | 9-253062 | 9/1997 |
| JP | 9-299342 | 11/1997 |
| JP | 2000-116611 | 4/2000 |
| JP | 2001-025462 | 1/2001 |
| JP | 2003-159221 | 6/2003 |
| JP | 2004-513750 A | 5/2004 |
| JP | 2004-283523 | 10/2004 |
| JP | 2007-044203 | 2/2007 |
| JP | 2007-185348 | 7/2007 |
| JP | 2008-136556 A | 6/2008 |
| JP | 2008-279061 A | 11/2008 |
| JP | 2009-153664 A | 7/2009 |
| JP | 2010-526646 | 8/2010 |
| JP | 2014-068733 A | 4/2014 |
| KR | 20-0204510 Y1 | 11/2000 |
| WO | WO 00/24064 | 4/2000 |
| WO | WO 00/047108 A1 | 8/2000 |
| WO | WO 01/08552 A1 | 2/2001 |
| WO | WO 2002/017782 A2 | 3/2002 |
| WO | WO 2005/010568 A2 | 2/2005 |
| WO | WO 2005/020121 A1 | 3/2005 |
| WO | WO 2005/110238 A1 | 11/2005 |
| WO | WO 2006/009830 A2 | 1/2006 |
| WO | WO 2006/067690 A2 | 6/2006 |
| WO | WO 2007/012931 A2 | 2/2007 |
| WO | WO 2007/053146 A1 | 5/2007 |
| WO | WO 2008/141306 A2 | 11/2008 |
| WO | 2009032074 A1 | 3/2009 |
| WO | WO 2013/019494 A2 | 2/2013 |
| WO | WO 2013/038296 A1 | 3/2013 |
| WO | WO 2013/109389 A1 | 7/2013 |
| WO | WO 2013/109390 A1 | 7/2013 |
| WO | WO 2014/092932 A1 | 6/2014 |

OTHER PUBLICATIONS

"Communication with European Search Report", EP Application No. 21151461.7, dated Apr. 30, 2021, 8 pp.

"U.S. Army Fitness Training Handbook" by the Department of the Army, 2003, The Lyons Press, p. 17.

"Warfighter Physiological and Environmental Monitoring: A Study for the U.S. Army Research Institute in Environmental Medicine and the Soldier Systems Center", Massachusetts Institute of Technology Lincoln Laboratory, Final Report, Nov. 1, 2004, prepared for the U.S. Army under Air Force Contract F19628-00-C-0002; approved for public release.

Anpo et al. "Photocatalytic Reduction of $Co_2$ With $H_2O$ on Titanium Oxides Anchored within Micropores of Zeolites: Effects of the Structure of the Active Sites and the Addition of Pt" *J. Phys. Chem. B*, 101:2632-2636 (1997).

Bârsan et al. "Understanding the fundamental principles of metal oxide based gas sensors; the example of CO sensing with $SnO_2$ sensors in the presence of humidity" *Journal of Physics: Condensed Matter* 15:R813-R839 (2003).

Bott "Electrochemistry of Semiconductors" *Current Separations* 17(3):87-91 (1998).

Colligan, M. J. et al. in "The psychological effects of indoor air pollution", Bulletin of the New York Academy of Medicine, vol. 57, No. 10, Dec. 1981, p. 1014-1026.

De Paula Santos, U. et al., in "Effects of air pollution on blood pressure and heart rate variability: a panel study of vehicular traffic controllers in the city of Sao Paulo, Brazil", European Heart Journal (2005) 26, 193-200.

Ebert, T et al., "Influence of Hydration Status on Thermoregulation and Cycling Hill Climbing," Med. Sci. Sport Exerc. vol. 39, No. 2, pp. 323-329, 2007.

Edmison et al., "E-Textile Based Automatic Activity Diary for Medical Annotation and Analysis," Proc. BSN 2006 Int. Workshop Wearable Implantable Body Sensor Netw. (2006), pp. 131-145, Apr. 3-5, 2006.

European Search Report corresponding to European Application No. 07862660.3 dated Apr. 25, 2012; 7 pages.

Falkner et al, "Cardiovascular response to mental stress in normal adolescents with hypertensive parents. Hemodynamics and mental stress in adolescents," *Hypertension* 1979, 1:23-30.

FITRAINER "The Only Trainer You Need"; http://itami.com: Downloaded Feb. 26, 2010; © 2008 FiTriainer™; 2 pages.

(56) References Cited

OTHER PUBLICATIONS

Fleming et al., "A Comparison of Signal Processing Techniques for the Extraction of Breathing Rate from the Photopethysmorgram," World Academy of Science, Engineering and Technology, vol. 30, Oct. 2007, pp. 276-280.
Geladas et al., "Effect of cold air inhalation on core temperature in exercising subjects under stress," The American Physiological Society, pp. 2381-2387, 1988.
Gibbs et al., "Reducing Motion Artifact Reduction for Wearable Sensors Using MEMS Accelerometers for Active Noise Cancellation," 2005 American Control Conference, Jun. 8-10, 2005, Portland, OR, USA, pp. 1581-1586.
Gold, D.R. et al. in "Ambient Pollution and Heart Rate Variability", Circulation 2000, 101:1267-1273.
International Search Report corresponding to International Patent Application No. PCT/US2012/046446, dated Jan. 14, 2013, 3 pages.
International Search Report and Written Opinion of the International Searching Authority, corresponding to PCT/US2012/0948079, dated Oct. 9, 2012.
International Search Report and Written Opinion of the International Searching Authority, corresponding to PCT/US2007/025114, dated May 13, 2008.
International Search Report Corresponding to International Application No. PCT/US2012/022634, dated Aug. 22, 2012, 9 pages.
Maomao et al., "Mobile Context-Aware Game for the Next Generation," $2^{nd}$ International Conference on Application and Development of ComputerGames ADCOG 2003, p. 78-81.
Martins et al. "Zinc oxide as an ozone sensor" Journal of Applied Physics 96(3): 1398-1408 (2004).
Maughan, R.J., "Impact of mild dehydration on wellness and on exercise performance," European Journal of Clinical Nutrition, 57, Suppl. 2, pp. S19-S23, 2003.
Maughan et al., "Exercise, Heat, Hydration and the Brain," Journal of the American College of Nutrition, vol. 26, No. 5, p. 604S-612S, 2007.
Mostardi, R., et al., "The effect of increased body temperature due to exercise on the heart rate and the maximal aerobic power," Europ. J. Appl. Physiol, 33, pp. 237-245, 1974.
Nakajima et al., "Monitoring of heart and respiratory rates by photoplethyusmography using a digital filtering technique," Med. Eng. Phys., vol. 18, No. 5, Jul. 1996, pp. 365-372.
Notification Concerning Transmittal of International Preliminary Report on Patentability, PCT/US2014/012909, dated Jul. 28, 2015.
Notification of Transmittal of the International Search Report and Written Opinion of the International Search Authority dated Jul. 30, 2010 by the Korean Intellectual Property Office for corresponding International Application No. PCT/US2010/021936.
Notification of Transmittal of the International Search Report and Written Opinion of the International Search Authority dated Aug. 26, 2010 by the Korean Intellectual Property Office for corresponding International Application No. PCT/US2010/021629.
Notification of Transmittal of the International Search Report and the Written Opinion of the International Search Authority dated Sep. 16, 2010 by the Korean Intellectual Property Office for corresponding International Application No. PCT/US2010/024922.
Notification of Transmittal of the International Search Report and the Written Opinion of the International Search Authority dated Sep. 27, 2010 by the Korean Intellectual Property Office for corresponding International Application No. PCT/US2010/025216.
Notification of Transmittal of The International Search Report and the Written Opinion of the International Searching Authority, or the Declaration corresponding to International Application No. PCT/US2013/070271; dated Feb. 26, 2014; 13 pages.
Saladin et al. "Photosynthesis of $CH_4$ at a $TiO_2$ Surface from Gaseous $H_2O$ and $CO_2$" J. Chem. Soc., Chem. Commun. 533-534 (1995).
Shorten et al., "Acute effect of environmental temperature during exercise on subsequent energy intake in active men," Am. J Clin. Nutr. 90, pp. 1215-21, 2009.

Skubal et al. "Detection and identification of gaseous organics using a $TiO_2$ sensor" Journal of Photochemistry and Photobiology A: Chemistry 148:103-108 (2002).
Skubal et al. "Monitoring the Electrical Response of Photoinduced Organic Oxideation on $TiO_2$ Surfaces" Manuscript submitted Oct. 2000 to SPIE Intl. Symposium on Environment & Industrial Sensing, Boston, MA, Nov. 5-8, 2000, sponsored by SPIE, 10 pp.
Thompson, M.W., "Cardiovascular drift and critical core temperature: factors limiting endurance performance in the heat?" J. Exerc. Sci. Fit, vol. 4, No. 1, pp. 15-24, 2006.
Wood et al., "Active Motion Artifact Reduction for Wearable Sensors Using Laguerre Expansion and Signal Separator," Proceedings of the 2005 IEEE Engineering in Medicine and Biology, $27^{th}$ Annual Conference, Shanghai, China, Sep. 1-4, 2005, pp. 3571-3574.
Zhang et al. "Development of Chemical Oxygen Demand On-Line Monitoring System Based on a Photoelectrochemical Degradation Principle" Environ. Sci. Technol., 40(7):2363 -2368 (2006).
European Search Report, EP Application No. 13863449.8, dated Oct. 19, 2015, 3 pages.
European Search Report, EP Application No. 14743615.8, dated Oct. 12, 2015, 3 pages.
European Search Report, EP Application No. 14743839.4, dated Oct. 12, 2015, 3 pages.
Gibbs et al., "Reducing Motion Artifact in Wearable Bio-Sensors Using MEMS Accelerometers for Active Noise Cancellation," 2005 American Control Conference, Jun. 8-10, 2005, Portland, OR, USA, pp. 1581-1586.
International Preliminary Report on Patentability, PCT/US2014/012940, dated Jun. 17, 2015, 23 pages.
International Search Report and Written Opinion of the International Searching Authority, corresponding to International Patent Application No. PCT/US2014/012940, dated Oct. 16, 2014, 13 pages.
International Search Report corresponding to International Patent Application No. PCT/US2014/012909, dated May 13, 2014, 3 pages.
Notification of Transmittal of the International Search Report and the Written Opinion of the International Searching Authority, or the Declaration, PCT/US2015/014562, dated Oct. 28, 2015.
Notification of Transmittal of the International Search Report and the Written Opinion of the International Searching Authority, or the Declaration, PCT/US2015/042636, dated Oct. 29, 2015.
Notification of Transmittal of the International Search Report and the Written Opinion of the International Searching Authority, or the Declaration, PCT/US2015/042015, dated Oct. 29, 2015.
Notification of Transmittal of the International Search Report and the Written Opinion of the International Searching Authority, or the Declaration, PCT/US2015/042035, dated Oct. 29, 2015.
Wood et al., "Active Motion Artifact Reduction for Wearable Sensors Using Laguerre Expansion and Signal Separation," Proceedings of the 2005 IEEE Engineering in Medicine and Biology, $27^{th}$ Annual Conference, Shanghai, China, Sep. 1-4, 2005, pp. 3571-3574.
Notification of Transmittal of the International Search Report and the Written Opinion of the International Searching Authority, or the Declaration, PCT/US2015/046079, dated Dec. 29, 2015.
Communication pursuant to Article 94(3) EPC, European Patent Application No. 13863449,8, dated Nov. 5, 2015, 7 pages.
Communication pursuant to Article 94(3) EPC, European Patent Application No. 14743615.8, dated Dec. 23, 2015, 7 pages.
Communication pursuant to Article 94(3) EPC, European Patent Application No. 14743839.4, dated Dec. 23, 2015, 6 pages.
Communication pursuant to Article 94(3) EPC, European Patent Application No. 12820308.0, dated Feb. 3, 2016, 5 pages.
Notification of Transmittal of the International Search Report and Written Opinion of the International Search Authority dated May 26, 2016 by the Korean Intellectual Property Office for corresponding International Application No. PCT/US2016/019126.
Notification of Transmittal of the International Search Report and Written Opinion of the International Search Authority dated May 26, 2016 by the Korean Intellectual Property Office for corresponding International Application No. PCT/US2016/019132.

(56) References Cited

OTHER PUBLICATIONS

Asada, et al., "Mobile Monitoring with Wearable Photoplethysmographic Biosensors," IEEE Engineering in Medicine and Biology Magazine, May/Jun. 2003, pp. 28-40.

Bifulco et al., "Bluetooth Portable Device for Continuous ECG and Patient Motion Monitoring During Daily Life," Medicon 2007, IFMBE Proceedings 16, 2007, pp. 369-372.

Brodersen et al., "In-Ear Acquisition of Vital Signs Discloses New Chances for Preventive Continuous Cardiovascular Monitoring," 4th International Workshop on Wearable and Implantable Body Sensor Networks (BSN 2007), vol. 13 of the series IFMBE Proceedings, pp. 189-194.

Celka et al, "Motion Resistant Earphone Located Infrared based Heart Rate Measurement Device," Proceedings of the Second IASTED International Conference on Biomedical Engineering, Feb. 16-18, 2004, Innsbruck, Austria, pp. 582-585.

Communication Pursuant to Article 94(3) EPC, EP 12 739 502.8, dated Jul. 19, 2016, 7 pages.

Communication Pursuant to Article 94(3) EPC, EP 14 743 615.8, dated Jul. 19, 2016, 7 pages.

Communication Pursuant to Article 94(3) EPC, EP 14 743 839.4, dated Jul. 20, 2016, 5 pages.

Comtois et al., "A Wearable Wireless Reflectance Pulse Oximeter for Remote Triage Applications," 2006 IEEE, pp. 53-54.

Comtois, Gary, W., "Implementation of Accelerometer-Based Adaptive Noise Cancellation in a Wireless Wearable Pulse Oximeter Platform for Remote Physiological Monitoring and Triage," Thesis, Worcester Polytechnic Institute, Aug. 31, 2007, 149 pages.

Duun et al., "A Novel Ring Shaped Photodiode for Reflectance Pulse Oximetry in Wireless Applications," IEEE Sensors 2007 Conference, pp. 596-599.

Geun et al., "Measurement Site and Applied Pressure Consideration in Wrist Photoplethysmography," The $23^{rd}$ International Technical Conference on Circuits/Systems, Computersand Communications, 2008, pp. 1129-1132.

Gibbs et al., "Active motion artifact cancellation for wearable health monitoring sensors using collocated MEMS accelerometers," Smart Structures and Materials, 2005: Sensors and Smart Structures Technologies for Civil, Mechanical, and Aerospace Systems, Proc. of SPIE, vol. 5765, pp. 811-819.

Haahr et al., "A Wearable "Electronic Patch" for Wireless Continuous Monitoring of Chronically Diseased Patients," Proceedings of the $5^{th}$ International Workshop on Wearable and Implantable Body Sensor Networks, in conjunction with the $5^{th}$ International Summer School and Symposium on Medical Devices and Biosensors, The Chinese University of Hong Kong, HKSAR, China, Jun. 1-3, 2008, pp. 66-70.

Jiang, Honghui, "Motion-Artifact Resistant Design of Photoplethysmograph Ring Sensor for Driver Monitoring," Thesis, Massachusetts Institute of Technology, Feb. 2004, 62 pages.

Kuzmina et al., "Compact multi-functional skin spectrometry set-up," Advanced Optical Materials, Technologies, and Devices, Proc. of SPIE, vol. 6596, 2007, pp. 65960T-1 to 65960T-6.

Lee et al, "Respiratory Rate Detection Algorithms by Photoplethysmography Signal Processing," $30^{th}$ Annual International IEEE EMBS Conference, Vancouver, British Columbia, Canada, Aug. 20-24, 2008, pp. 1140-1143.

Lindberg et al., "Monitoring of respiratory and heart rates using a fibre-optic sensor," Med Biol Eng Comput, Sep. 1992, vol. 30, No. 5, pp. 533-537.

Luprano, Jean, "Sensors and Parameter Extraction by Wearable Systems: Present Situation and Future," pHealth 2008, May 21, 2008, 29 pages.

Lygouras et al., "Optical-Fiber Finger Photo-Plethysmograph Using Digital Techniques," IEEE Sensors Journal, vol. 2, No. 1, Feb. 2002, pp. 20-25.

Maguire et al., "The Design and Clinical Use of a Reflective Brachial Photoplethysmograph," Technical Report NUIM/SS/—/2002/04, Submitted Apr. 2002, Signals and Systems Research Group, National University of Ireland, Maynooth, Co. Kildare, Ireland, 13 pages.

Mendelson et al., "Measurement Site and Photodetector Size Considerations in Optimizing Power Consumption of a Wearable Reflectance Pulse Oximeter," Proceedings of the $25^{th}$ Annual International Conference of the IEEE EMBS, Cancun, Mexico, Sep. 17-21, 2003, pp. 3016-3019.

Mendelson et al., "Noninvasive Pulse Oximetry Utilizing Skin Reflectance Photoplethysmography," IEEE Transactions on Biomedical Engineering, vol. 35, No. 10, Oct. 1988, pp. 798-805.

Poh et al., "Motion Tolerant Magnetic Earring Sensor and Wireless Earpiece for Wearable Photoplethysmography," IEEE Transactions on Information Technology in Biomedicine, vol. 14, No. 3, May 2010, pp. 786-794.

Renevey et al., "Wrist-Located Pulse Detection Using IR Signals, Activity and Nonlinear Artifact Cancellation," IEEE EMBS, 2001, 4 pages.

Rhee et al., "Artifact-Resistant Power-Efficient Design of Finger-Ring Plethysmographic Sensors," IEEE Transactions on Biomedical Engineering, vol. 48, No. 7, Jul. 2001, pp. 795-805.

Shaltis, Phillip Andrew, Analysis and Validation of an Artifact Resistant Design for Oxygen Saturation Measurement Using Photo Plethysmographic Ring Sensors, Thesis, Massachusetts Institute of Technology, Jun. 2004, 103 pages.

Shin et al., "A Novel Headset with a Transmissive PPG Sensor for Heart Rate Measurement," ICBME 2008, Proceedings 23, 2009, pp. 519-522.

Spigulis et al, "Wearable wireless photoplethysmography sensors," Proc. of SPIE, vol. 6991, 2008, pp. 69912O-1 to 69912O-7.

Takatani et al., "Optical Oximetry Sensors for Whole Blood and Tissue," IEEE Engineering in Medicine and Biology, Jun./Jul. 1994, pp. 347-357.

Vogel et al., "A System for Assessing Motion Artifacts in the Signal of a Micro-Optic In-Ear Vital Signs Sensor," $30^{th}$ Annual International IEEE EMBS Conference, Vancouver, British Columbia, Canada, Aug. 20-24, 2008.

Vogel et al., "In-Ear Heart Rate Monitoring Using a Micro-Optic Reflective Sensor," Proceedings of the $29^{th}$ Annual International Conference of the IEEE EMBS Cite Internationale, Lyon, France, Aug. 23-26, 2007, pp. 1375-1378.

Wang et al., "Multichannel Reflective PPG Earpiece Sensor With Passive Motion Cancellation," IEEE Transactions on Biomedical Circuits and Systems, vol. 1, No. 4, Dec. 2007, pp. 235-241.

Wang et al., "Reflective Photoplethysmograph Earpiece Sensor for Ubiquitous Heart Rate Monitoring," $4^{th}$ International Workshop on Wearable and Implantable Body Sensor Networks, 2007, vol. 13 of the series IFMBE Proceedings, pp. 179-183.

Wei et al. "A New Wristband Wearable Sensor Using Adaptive Reduction Filter to Reduce Motion Artifact," Proceedings of the $5^{th}$ International Conference on Information Technology and Application in Biomedicine, in conjunction with the $2^{nd}$ International Symposium & Summer School on Biomedical and Health Engineering, Shenzhen, China, May 30-31, 2008, pp. 278-281.

Wood, Levi Benjamin, "Motion Artifact Reduction for Wearable Photoplethysmogram Sensors Using Micro Accelerometers and Laguerre Series Adaptive Filters," Thesis, Massachusetts Institute of Technology, Jun. 2008, 74 pages.

Han et al., "Artifacts in wearable photoplethysmographs during daily life motions and their reduction with least mean square based active noise cancellation method," Computers in Biology and Medicine, 42, 2012, pp. 387-393.

Extended European Search Report, EP Application No. 16164775.5 dated Sep. 13, 2016, 7 pages.

Notification of Transmittal of the International Search Report and the Written Opinion of the International Searching Authority, or the Declaration, PCT/US2016/041842, dated Oct. 21, 2016, 5 pages.

Notification of Transmittal of International Preliminary Report on Patentability, PCT/US2015/041562, dated Oct. 20, 2016, 14 pages.

Notification of Transmittal of International Preliminary Report on Patentability, PCT/US2015/042636, dated Oct. 20, 2016, 7 pages.

Notification of Transmittal of International Preliminary Report on Patentability, PCT/US2015/042015, dated Oct. 20, 2016, 10 pages.

(56) References Cited

OTHER PUBLICATIONS

Notification of Transmittal of International Preliminary Report on Patentability, PCT/US2015/042035, dated Oct. 20, 2016, 8 pages.
Notification of Transmittal of International Preliminary Report on Patentability, PCT/US2015/046079, dated Oct. 20, 2016, 10 pages.
Communication with Supplementary European Search Report, EP Application No. 15826541.3, dated Jul. 10, 2017, 8 pp.
Communication with Supplementary European Search Report, EP Application No. 15827188.2, dated Jul. 10, 2017, 7 pp.
Lee et al., "Comparison Between Red, Green and Blue Light Reflection PPG for Heart Rate Monitoring During Motion", Conf. Proc. IEEE Eng. Med. Biol. Soc., pp. 1724-7, 2013.
Maeda et al., "The Advantages of Wearable Green Reflected PPG", J. Med. Syst., pp. 829-834, 2011.
Tamura et al., "Wearable PPG Sensors-Past and Present", Electronics, pp. 282-302, 2014.

\* cited by examiner

| Parameter | Subject 1 250 Hz | Subject 1 125 Hz | Subject 1 25 Hz | Subject 2 250 Hz | Subject 2 125 Hz | Subject 2 25 Hz |
|---|---|---|---|---|---|---|
| Median (ms) | 868 | 870 | 880 | 714 | 716 | 720 |
| Mean (ms) | 862 | 862 | 865 | 740 | 740 | 734 |
| SD (ms) | 161 | 165 | 167 | 130 | 132 | 121 |
| NN50 | 43 | 42 | 31 | 31 | 35 | 45 |

PHYSIOLOGICAL MONITORING DEVICES AND METHODS USING OPTICAL SENSORS

RELATED APPLICATIONS

This application is a continuation application of pending U.S. patent application Ser. No. 16/503,191, filed Jul. 3, 2019, which is a continuation application of pending U.S. patent application Ser. No. 14/807,149, filed Jul. 23, 2015, and which claims the benefit of and priority to U.S. Provisional Patent Application No. 62/030,951 filed Jul. 30, 2014, and U.S. Provisional Patent Application No. 62/109,196 filed Jan. 29, 2015, the disclosures of which are incorporated herein by reference as if set forth in their entireties.

FIELD OF THE INVENTION

The present invention relates generally to monitoring devices and, more particularly, to monitoring devices for measuring physiological information.

BACKGROUND OF THE INVENTION

Photoplethysmography (PPG) is based upon shining light into the human body and measuring how the scattered light intensity changes with each pulse of blood flow. The scattered light intensity will change in time with respect to changes in blood flow or blood opacity associated with heart beats, breaths, blood oxygen level ($SpO_2$), and the like. Such a sensing methodology may require the magnitude of light energy reaching the volume of flesh being interrogated to be steady and consistent so that small changes in the quantity of scattered photons can be attributed to varying blood flow. If the incidental and scattered photon count magnitude changes due to light coupling variation between the source or detector and the skin or other body tissue, then the signal of interest can be difficult to ascertain due to large photon count variability caused by motion artifacts. Changes in the surface area (and volume) of skin or other body tissue being impacted with photons, or varying skin surface curvature reflecting significant portions of the photons may also significantly impact optical coupling efficiency. Physical activity, such a walking, cycling, running, etc., may cause motion artifacts in the optical scatter signal from the body, and time-varying changes in photon intensity due to motion artifacts may swamp-out time-varying changes in photon intensity due to blood flow changes. Each of these changes in optical coupling can dramatically reduce the signal-to-noise ratio (S/N) of biometric PPG information to total time-varying photonic interrogation count. This can result in a much lower accuracy in metrics derived from PPG data, such as heart rate and breathing rate.

An earphone, such as a headset, earbud, etc., may be a good choice for incorporation of a photoplethysmograph device because it is a form factor that individuals are familiar with, it is a device that is commonly worn for long periods of time, and it frequently is used during exercise which is a time when individuals may benefit most from having accurate heart rate data (or other physiological data). Unfortunately, incorporation of a photoplethysmograph device into an earphone poses several challenges. For example, earphones may be uncomfortable to wear for long periods of time, particularly if they deform the ear surface. Moreover, human ear anatomy may vary significantly from person to person, so finding an earbud form that will fit comfortably in many ears may pose significant challenges. In addition, earbuds made for vigorous physical activity typically incorporate an elastomeric surface and/or elastomeric features to function as springs that dampen earbud acceleration within the ear. Although, these features may facilitate retention of an earbud within an ear during high acceleration and impact modalities, they may not adequately address optical skin coupling requirements needed to achieve quality photoplethysmography.

Conventional photoplethysmography devices, as illustrated for example in FIGS. 1A-1C, typically suffer from reduced skin coupling as a result of subject motion. For example, most conventional photoplethysmography devices use a spring to clip the sensor onto either an earlobe (FIG. 1A) or a fingertip (FIG. 1B). Unfortunately, these conventional devices tend to have a large mass and may not maintain consistent skin contact when subjected to large accelerations, such as when a subject is exercising.

A conventional earbud device that performs photoplethysmography in the ear is the MX-D100 player from Perception Digital of Wanchai, Hong Kong (www.perceptiondigital.com). This earbud device, illustrated in FIG. 1C and indicated as 10, incorporates a spring biased member 12 to improve PPG signal quality. The member 12 is urged by a spring or other biasing element (not shown) in the direction of arrow $A_1$, as indicated in FIG. 1C. The spring biased member 12 forcibly presses the entire earbud 10 within the ear E of a subject to minimize motion of the entire earbud 10. However, there are several drawbacks to the device 10 of FIG. 1C. For example, the source/sensor module is coupled to the entire earbud mass and, as such, may experience larger translation distances resulting in greater signal variability when the ear undergoes accelerations. In addition, because the earbud 10 is held in place with one primary spring force direction, significant discomfort can be experienced by the end user. Moreover, the earbud motion is only constrained in one direction (i.e., the direction indicated by $A_1$) due to the single spring force direction.

Because PPG used in wearable devices employs an optical technology, requiring the powering of optical emitters and microprocessors via a wearable battery, managing power consumption can be challenging. For example, high-power algorithms may be required to accurately measure heart rate during exercise. Thus, employing a high-power algorithm during exercise may have the benefit of accurately monitoring heart rate during exercise but may also have the unwanted effect of draining the battery of the wearable device such that the device will not have enough power to measure a subject over the course of a day or week during non-exercising periods.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a monitoring device configured to be attached to a body of a subject includes a sensor that is configured to detect and/or measure physiological information from the subject and a processor coupled to the sensor that is configured to receive and analyze signals produced by the sensor. The sensor may be an optical sensor that includes at least one optical emitter and at least one optical detector, although various other types of sensors may be utilized. The processor is configured to change the signal analysis frequency (i.e., the signal sampling rate), sensor algorithm, and/or sensor interrogation power in response to detecting a change in subject activity. For example, in some embodiments, the processor increases signal analysis frequency and/or sensor interrogation power in response to detecting an increase in subject activity, and decreases signal analysis frequency and/or sensor interrogation power in response to detecting a decrease in subject activity. In other embodiments, the processor may change the sensor algorithm in response to a change in subject activity. For example, the processor may implement frequency-domain digital signal processing in response to detecting high subject activity, and implement time-domain digital signal processing in response to detecting low subject activity. The frequency- and time-domain algorithms represent two different signal extraction methods for extracting accurate biometrics from optical sensor signals, where the frequency-domain algorithm may require substantially greater processing power than that of the time-domain algorithm.

In some embodiments, detecting a change in subject activity comprises detecting a change in at least one subject vital sign, such as subject heart rate, subject blood pressure, subject temperature, subject respiration rate, subject perspiration rate, etc. In other embodiments, the sensor includes a motion sensor, such as an accelerometer, gyroscope, etc., and detecting a change in subject activity includes detecting a change in subject motion via the motion sensor. In some embodiments, detecting a change in subject activity may include predicting a type of activity the subject is engaged in.

According to some embodiments of the present invention, a method of monitoring a subject via a monitoring device having a sensor includes changing signal analysis frequency and/or sensor interrogation power in response to detecting a change in subject activity. In some embodiments, detecting a change in subject activity comprises detecting a change in at least one subject vital sign, such as subject heart rate, subject blood pressure, subject temperature, subject respiration rate, and/or subject perspiration rate, etc. In other embodiments, detecting a change in subject activity comprises detecting a change in subject motion via a motion sensor associated with the sensor.

In some embodiments, changing signal analysis frequency and/or sensor interrogation power in response to detecting a change in subject activity includes increasing signal analysis frequency and/or sensor interrogation power in response to detecting an increase in subject activity, and decreasing signal analysis frequency and/or sensor interrogation power in response to detecting a decrease in subject activity. In other embodiments, the processor is configured to implement frequency-domain digital signal processing in response to detecting high subject activity, and to implement time-domain digital signal processing in response to detecting low subject activity.

According to other embodiments of the present invention, a monitoring device configured to be attached to a subject includes a sensor configured to detect and/or measure physiological information from the subject. The monitoring device also includes a processor coupled to the sensor that is configured to receive and analyze signals produced by the sensor. The sensor may be an optical sensor that includes at least one optical emitter and at least one optical detector, although various other types of sensors may be utilized. The processor is configured to change signal analysis frequency and/or sensor interrogation power in response to detecting, via the sensor or another sensor, a change in the at least one environmental condition, such as temperature, humidity, air quality, barometric pressure, radiation, light intensity, and sound. For example, in some embodiments, the processor increases signal analysis frequency and/or sensor interrogation power in response to detecting an increase in the at least one environmental condition, and decreases signal analysis frequency and/or sensor interrogation power in response to detecting a decrease in the at least one environmental condition.

In some embodiments, a method of monitoring a subject via a monitoring device includes changing signal analysis frequency and/or sensor interrogation power in response to detecting a change in at least one environmental condition. For example, in some embodiments, changing signal analysis frequency and/or sensor interrogation power in response to detecting a change in at least one environmental condition includes increasing signal analysis frequency and/or sensor interrogation power in response to detecting an increase in at least one environmental condition, and decreasing signal analysis frequency and/or sensor interrogation power in response to detecting a decrease in at least one environmental condition.

According to other embodiments of the present invention, a monitoring device configured to be attached to a subject includes a clock (e.g., a digital clock, an internal software clock, etc.) or is in communication with a clock, a sensor configured to detect and/or measure physiological information from the subject, and a processor coupled to the clock and the sensor. The sensor may be an optical sensor that includes at least one optical emitter and at least one optical detector, although various other types of sensors may be utilized. The processor is configured to receive and analyze signals produced by the sensor, and is configured to change signal analysis frequency and/or sensor interrogation power at one or more predetermined times. For example, in some embodiments, the processor increases signal analysis frequency and/or sensor interrogation power at a first time, and decreases signal analysis frequency and/or sensor interrogation power at a second time. In other embodiments, the processor adjusts signal analysis frequency and/or sensor interrogation power according to a circadian rhythm of the subject.

According to some embodiments, a method of monitoring a subject via a monitoring device includes changing signal analysis frequency and/or sensor interrogation power at one or more predetermined times. In some embodiments, changing signal analysis frequency and/or sensor interrogation power at one or more predetermined times includes increasing signal analysis frequency and/or sensor interrogation power at a first time, and decreasing signal analysis frequency and/or sensor interrogation power at a second time. In other embodiments, changing signal analysis frequency and/or sensor interrogation power at one or more predetermined times comprises adjusting signal analysis frequency and/or sensor interrogation power according to a circadian rhythm of the subject.

According to other embodiments of the present invention, a monitoring device configured to be attached to a subject includes a location sensor or is in communication with a location sensor, a sensor configured to detect and/or measure physiological information from the subject, and a processor coupled to the location sensor and the sensor. The sensor may be an optical sensor that includes at least one optical emitter and at least one optical detector, although various other types of sensors may be utilized. The processor is configured to receive and analyze signals produced by the sensor and to change signal analysis frequency and/or sensor interrogation power when the subject has changed locations.

For example, in some embodiments, the processor increases signal analysis frequency and/or sensor interrogation power when the subject is at a particular location, and decreases signal analysis frequency and/or sensor interrogation power when the subject is no longer at the particular location According to some embodiments, a method of monitoring a subject via a monitoring device includes changing signal analysis frequency and/or sensor interrogation power when a location sensor associated with the monitoring device indicates the subject has changed locations. For example, in some embodiments, signal analysis frequency and/or sensor interrogation power is increased when the subject is at a particular location, and signal analysis frequency and/or sensor interrogation power is decreased when the subject is no longer at the particular location.

According to other embodiments of the present invention, a monitoring device configured to be attached to a subject includes a sensor configured to detect and/or measure physiological information from the subject, and a processor coupled to the sensor. The sensor includes at least one optical emitter and at least one optical detector. The processor is configured to receive and analyze signals produced by the sensor, and is configured to change the wavelength of light emitted by the at least one optical emitter in response to detecting a change in subject activity. In some embodiments, the processor instructs the at least one optical emitter to emit shorter wavelength light (e.g., a decrease in wavelength by 100 nm or more) in response to detecting an increase in subject activity, and instructs the at least one optical emitter to emit longer wavelength light (e.g., an increase in wavelength by 100 nm or more) in response to detecting an decrease in subject activity.

In some embodiments, detecting a change in subject activity comprises detecting a change in at least one subject vital sign, such as subject heart rate, subject blood pressure, subject temperature, subject respiration rate, subject perspiration rate, etc. In other embodiments, the sensor includes a motion sensor, such as an accelerometer, gyroscope, etc., and detecting a change in subject activity includes detecting a change in subject motion via the motion sensor.

In some embodiments, detecting a change in subject activity may include predicting a type of activity the subject is engaged in.

According to some embodiments of the present invention, a method of monitoring a subject via a monitoring device having a sensor includes changing wavelength of light emitted by at least one optical emitter associated with the sensor in response to detecting a change in subject activity. For example, in some embodiments, changing wavelength of light emitted by the at least one optical emitter may include instructing the at least one optical emitter to emit shorter wavelength light in response to detecting an increase in subject activity, and instructing the at least one optical emitter to emit longer wavelength light in response to detecting an decrease in subject activity.

According to other embodiments of the present invention, a monitoring device configured to be attached to a subject includes a sensor configured to detect and/or measure physiological information from the subject, and a processor coupled to the sensor and configured to receive and analyze signals produced by the sensor. The sensor comprises at least one optical emitter and at least one optical detector, and the processor instructs the at least one optical emitter to emit a different wavelength of light during each of a series of respective time intervals such that a respective different physiological parameter can be measured from the subject during each time interval via the at least one optical detector.

According to some embodiments of the present invention, a method of monitoring a subject via a monitoring device having a sensor with at least one optical emitter and at least one optical detector comprises emitting a different wavelength of light during each of a series of respective time intervals, and measuring a respective different physiological parameter of the subject during each time interval via the at least one optical detector.

According to other embodiments of the present invention, a monitoring device configured to be attached to a subject includes a sensor configured to detect and/or measure physiological information from the subject, and a processor coupled to the sensor. The processor is configured to receive and analyze signals produced by the sensor, and is configured to change signal analysis frequency and/or change sensor interrogation power in response to detecting a change in subject stress level (e.g., by detecting a change in at least one subject vital sign, such as heart rate, blood pressure, temperature, respiration rate, and/or perspiration rate). For example, in some embodiments, the processor increases signal analysis frequency and/or increases sensor interrogation power in response to detecting an increase in subject stress level, and decreases signal analysis frequency and/or decreases sensor interrogation power in response to detecting a decrease in subject stress level.

In some embodiments, the sensor comprises a voice recognition system. The processor is configured to increase processing power for the voice recognition system in response to detecting an increase in subject stress level, and to decrease processing power for the voice recognition system in response to detecting an decrease in subject stress level.

In some embodiments, the sensor is in communication with a user interface. In some embodiments, the processor may be configured to increase user interface brightness and/or font size of alphanumeric characters displayed on the user interface in response to detecting an increase in subject stress level, and is configured to decrease user interface brightness and/or font size of alphanumeric characters displayed on the user interface in response to detecting a decrease in subject stress level. In some embodiments, the processor may be configured to enlarge an image displayed within the user interface and/or make an image displayed within the user interface easier to view/comprehend (e.g., increase the resolution of the image, etc.) in response to detecting an increase in subject stress level. The processor may be configured to decrease an image displayed within the user interface and/or reduce the resolution of an image displayed within the user interface in response to detecting an increase in subject stress level.

According to some embodiments of the present invention, a method of monitoring a subject via a monitoring device having a sensor includes changing signal analysis frequency and/or changing sensor interrogation power via the processor in response to detecting a change in subject stress level. For example, in some embodiments signal analysis frequency and/or sensor interrogation power is increased in response to detecting an increase in subject stress level, and signal analysis frequency and/or sensor interrogation power is decreased in response to detecting a decrease in subject stress level.

In some embodiments, the sensor comprises a voice recognition system, and the method includes increasing processing power for the voice recognition system in response to detecting an increase in subject stress level, and decreasing processing power for the voice recognition system in response to detecting a decrease in subject stress level.

In some embodiments, the sensor is in communication with a user interface, and the method includes increasing user interface brightness and/or font size of alphanumeric characters displayed on the user interface in response to detecting an increase in subject stress level, and decreasing user interface brightness and/or font size of alphanumeric characters displayed on the user interface in response to detecting a decrease in subject stress level.

According to other embodiments of the present invention, a method of monitoring a subject wearing a PPG sensor device having at least one processor includes processing PPG sensor readings via the at least one processor to determine if the subject is located indoors or outdoors, and selecting a PPG sensor polling routine associated with indoor or outdoor conditions depending on whether the subject is located indoors or outdoors, respectively. In some embodiments, if the subject is located indoors, the PPG sensor polling routine is configured to direct the PPG sensor to utilize light with at least one visible wavelength and at least one infrared (IR) wavelength, and if the subject is located outdoors, the PPG sensor polling routine is configured to direct the PPG sensor to utilize light with at least two distinct IR wavelengths or two different IR wavelength bands. The method may further include determining blood and/or tissue oxygenation of the subject via the PPG sensor.

Monitoring devices in accordance with some embodiments of the present invention may be configured to be positioned at or within an ear of a subject or secured to an appendage or other body location of the subject Monitoring devices, according to embodiments of the present invention, are advantageous over conventional monitoring devices because, by changing signal analysis frequency and/or sensor interrogation power, power savings may be incurred. Moreover, increasing sensing power or sampling frequency may allow for finer, more accurate sensor data to be collected during periods of rapid body activity, e.g., during exercising, running, walking, etc. Conversely sensor data changes during periods of inactivity maybe infrequent and require significantly lower power to achieve sufficient data resolution to accurately describe physiological changes.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

DETAILED DESCRIPTION

Figure 1A:
FIG. 1A is a perspective view of a conventional PPG device attached to the ear of a person.
Figure 1B:
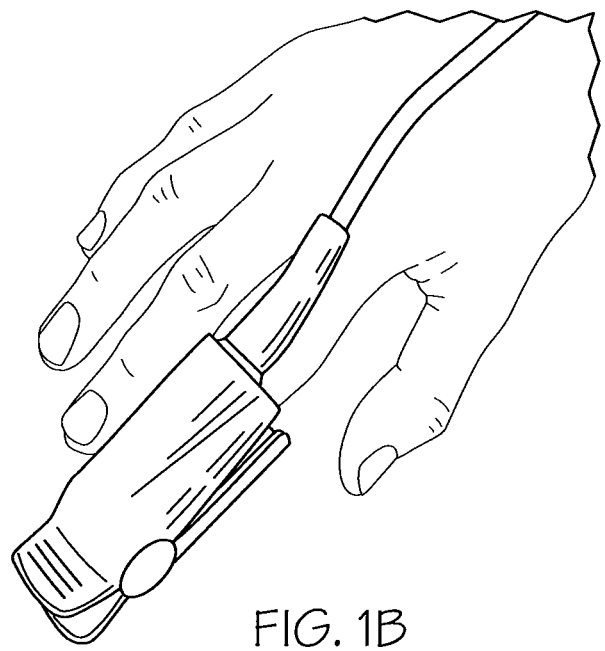
FIG. 1B is a perspective view of a conventional PPG device attached to a finger of a person.
Figure 1C:
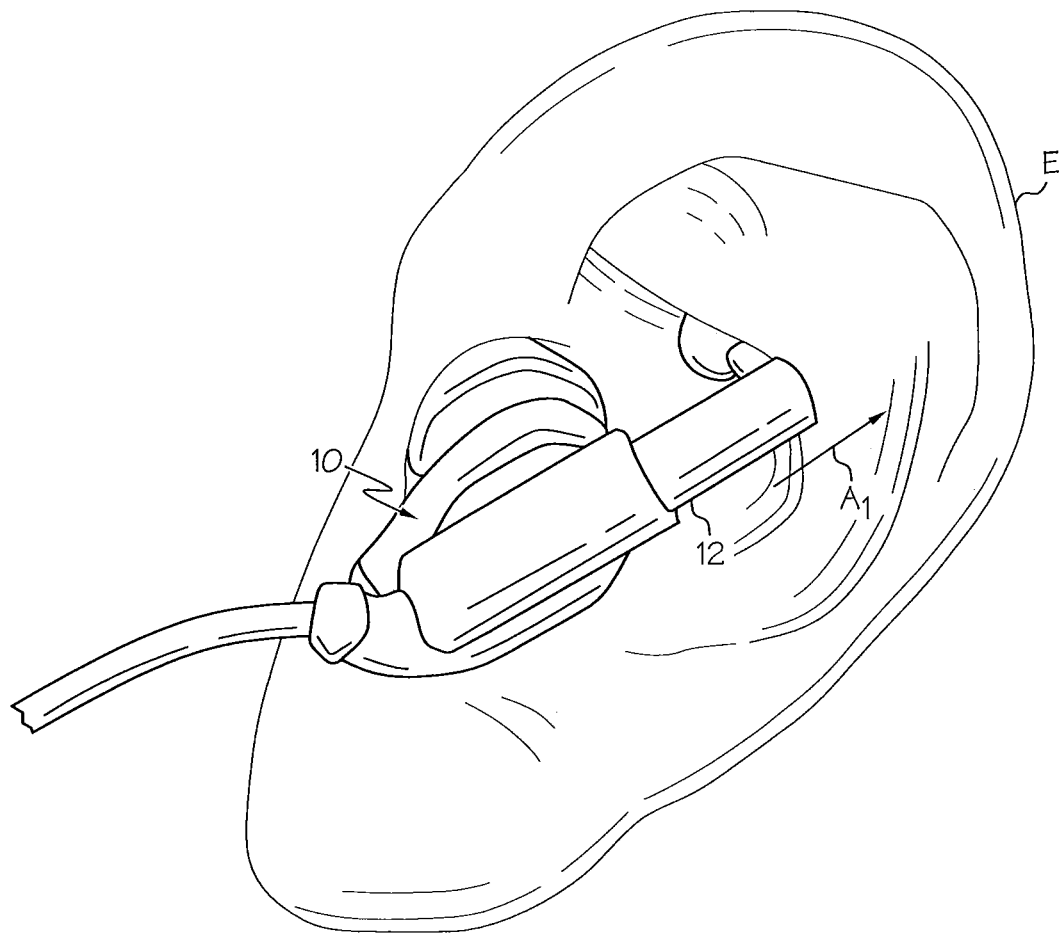
FIG. 1C illustrates a conventional PPG device attached to the ear of a person, and wherein a biasing element is utilized to retain the photoplethysmography device in the person's ear.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "secured", "connected", "attached" or "coupled" to another feature or element, it can be directly secured, directly connected, attached or coupled to the other feature or element or intervening features or elements may be present. In contrast, when a feature or element is referred to as being "directly secured", "directly connected", "directly attached" or "directly coupled" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

As used herein, the term "and/or" includes any and all combinations of one or more of the associated listed items and may be abbreviated as "/".

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features or elements, these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary more or less, for example by +/−20%, +/−10%, +/−5%, +/−1%, +/−0.5%, +/−0.1%, etc.

The terms "sensor", "sensing element", and "sensor module", as used herein, are interchangeable and refer to a sensor element or group of sensor elements that may be utilized to sense information, such as information (e.g., physiological information, body motion, etc.) from the body of a subject and/or environmental information in a vicinity of the subject. A sensor/sensing element/sensor module may comprise one or more of the following: a detector element, an emitter element, a processing element, optics, mechanical support, supporting circuitry, and the like. Both a single sensor element and a collection of sensor elements may be considered a sensor, a sensing element, or a sensor module.

The term "optical emitter", as used herein, may include a single optical emitter and/or a plurality of separate optical emitters that are associated with each other.

The term "optical detector", as used herein, may include a single optical detector and/or a plurality of separate optical detectors that are associated with each other.

The term "wearable sensor module", as used herein, refers to a sensor module configured to be worn on or near the body of a subject.

The terms "monitoring device" and "biometric monitoring device", as used herein, are interchangeable and include any type of device, article, or clothing that may be worn by and/or attached to a subject and that includes at least one sensor/sensing element/sensor module. Exemplary monitoring devices may be embodied in an earpiece, a headpiece, a finger clip, a digit (finger or toe) piece, a limb band (such as an arm band or leg band), an ankle band, a wrist band, a nose piece, a sensor patch, eyewear (such as glasses or shades), apparel (such as a shirt, hat, underwear, etc.), a mouthpiece or tooth piece, contact lenses, or the like.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "headset", as used herein, is intended to include any type of device or earpiece that may be attached to or near the ear (or ears) of a user and may have various configurations, without limitation. Headsets incorporating optical sensor modules, as described herein, may include mono headsets (a device having only one earbud, one earpiece, etc.) and stereo headsets (a device having two earbuds, two earpieces, etc.), earbuds, hearing aids, ear jewelry, face masks, headbands, and the like. In some embodiments, the term "headset" may include broadly headset elements that are not located on the head but are associated with the headset. For example, in a "medallion" style wireless headset, where the medallion comprises the wireless electronics and the headphones are plugged into or hard-wired into the medallion, the wearable medallion would be considered part of the headset as a whole. Similarly, in some cases, if a mobile phone or other mobile device is intimately associated with a plugged-in headphone, then the term "headset" may refer to the headphone-mobile device combination. The terms "headset" and "earphone", as used herein, are interchangeable.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature.

The term "body" refers to the body of a subject (human or animal) that may wear a monitoring device, according to embodiments of the present invention.

The term "processor" is used broadly to refer to a signal processor or computing system or processing or computing method which may be localized or distributed. For example, a localized signal processor may comprise one or more signal processors or processing methods localized to a general location, such as to a wearable device. Examples of such wearable devices may comprise an earpiece, a headpiece, a finger clip, a digit (finger or toe) piece, a limb band (such as an arm band or leg band), an ankle band, a wrist band, a nose piece, a sensor patch, eyewear (such as glasses or shades), apparel (such as a shirt, hat, underwear, etc.), a mouthpiece or tooth piece, contact lenses, or the like. Examples of a distributed processor comprise "the cloud", the internet, a remote database, a remote processor computer, a plurality of remote processors or computers in communication with each other, or the like, or processing methods distributed amongst one or more of these elements. The key difference is that a distributed processor may include delocalized elements, whereas a localized processor may work independently of a distributed processing system. As a specific example, microprocessors, microcontrollers, ASICs (application specific integrated circuits), analog processing circuitry, or digital signal processors are a few non-limiting examples of physical signal processors that may be found in wearable devices.

The term "remote" does not necessarily mean that a remote device is a wireless device or that it is a long distance away from a device in communication therewith. Rather, the term "remote" is intended to reference a device or system that is distinct from another device or system or that is not substantially reliant on another device or system for core functionality. For example, a computer wired to a wearable device may be considered a remote device, as the two devices are distinct and/or not substantially reliant on each other for core functionality. However, any wireless device (such as a portable device, for example) or system (such as a remote database for example) is considered remote to any other wireless device or system.

The terms "signal analysis frequency" and "signal sampling rate", as used herein, are interchangeable and refer to the number of samples per second (or per other unit) taken from a continuous sensor (i.e., physiological sensor and environmental sensor) signal to ultimately make a discrete signal. The term "sensor module interrogation power", as used herein, refers to the amount of electrical power required to operate one or more sensors (i.e., physiological sensors and environmental sensors) of a sensor module and/or any processing electronics or circuitry (such as microprocessors and/or analog processing circuitry) associated therewith. Examples of decreasing the sensor interrogation power may include lowering the voltage or current through a sensor element (such as lowering the voltage or current applied to a pair of electrodes), lowering the polling (or polling rate) of a sensor element (such as lowering the frequency at which an optical emitter is flashed on/off in a PPG sensor), lowering the sampling frequency of a stream of data (such as lowering the sampling frequency of the output of an optical detector in a PPG sensor), selecting a lower-power algorithm (such as selecting a power-efficient time-domain processing method for measuring heart rate vs. a more power-hungry frequency-domain processing method), or the like. Lowering the interrogation power may also include powering only one electrode, or powering less electrodes, in a sensor module or sensor element such that less total interrogation power is exposed to the body of a subject. For example, lowering the interrogation power of a PPG sensor may comprise illuminating only one light-emitting diode rather than a plurality of light-emitting diodes that may be present in the sensor module, and lowering the interrogation power of a bioimpedance sensor may comprise powering only one electrode pair rather than a plurality of electrodes that may be present in the bioimpedance sensor module.

The term "polling" typically refers to controlling the intensity of an energy emitter of a sensor or to the "polling rate" and/or duty cycle of an energy emitter element in a sensor, such as an optical emitter in a PPG sensor or an ultrasonic driver in an ultrasonic sensor. Polling may also refer to the process of collecting and not collecting sensor data at certain periods of time. For example, a PPG sensor may be "polled" by controlling the intensity of one or more optical emitters, i.e. by pulsing the optical emitter over time. Similarly, the detector of a PPG sensor may be polled by reading data from that sensor only at a certain point in time or at certain intervals, i.e., as in collecting data from the detector of a PPG sensor for a brief period during each optical emitter pulse. A sensor may also be polled by turning on or off one or more elements of that sensor in time, such as when a PPG sensor is polled to alternate between multiple LED wavelengths over time or when an ultrasonic sensor is polled to alternate between mechanical vibration frequencies over time.

The terms "sampling frequency", "signal analysis frequency", and "signal sampling rate", as used herein, are interchangeable and refer to the number of samples per second (or per other unit) taken from a continuous sensor or sensing element (for example, the sampling rate of the thermopile output in a tympanic temperature sensor).

It should be noted that processes for managing hysteresis are implied herein. Namely, several embodiments herein for controlling sensors (and other wearable hardware) may involve a processor sending commands to a sensor element depending on the sensor readings. Thus, in some embodiments, a sensor reading (such as a reading from an optical detector or a sensing electrode) above X may result in a processor sending a command to electrically bias another sensor element (such as an optical emitter or a biasing electrode) above Y. Similarly, as soon as the sensor reading drops below X, a processor may send a command to bias another sensor element below Y. However, in borderline situations this may cause unwanted hysteresis in the biasing command, as sensor readings may rapidly toggle above/below X resulting in the toggling of the biasing of another sensor element above/below Y. As such, hysteresis management may be integrated within the algorithm(s) for controlling the execution of a processor. For example, the processor may be configured by the algorithm to delay a biasing command by a period of time Z following the timing of a prior biasing command, thereby preventing or reducing the aforementioned toggling.

In the following figures, various monitoring devices will be illustrated and described for attachment to the ear or an appendage of the human body. However, it is to be understood that embodiments of the present invention are not limited to those worn by humans.

The ear is an ideal location for wearable health and environmental monitors. The ear is a relatively immobile platform that does not obstruct a person's movement or vision. Monitoring devices located at an ear have, for example, access to the inner-ear canal and tympanic membrane (for measuring core body temperature), muscle tissue (for monitoring muscle tension), the pinna, earlobe, and elsewhere (for monitoring blood gas levels), the region behind the ear (for measuring skin temperature and galvanic skin response), and the internal carotid artery (for measuring cardiopulmonary functioning), etc. The ear is also at or near the point of exposure to: environmental breathable toxicants of interest (volatile organic compounds, pollution, etc.); noise pollution experienced by the ear; and lighting conditions for the eye. Furthermore, as the ear canal is naturally designed for transmitting acoustical energy, the ear provides a good location for monitoring internal sounds, such as heartbeat, breathing rate, and mouth motion.

Optical coupling into the blood vessels of the ear may vary between individuals. As used herein, the term "coupling" refers to the interaction or communication between excitation energy (such as light) entering a region and the region itself. For example, one form of optical coupling may be the interaction between excitation light generated from within an optical sensor of an earbud (or other device positioned at or within an ear) and the blood vessels of the ear. In one embodiment, this interaction may involve excitation light entering the ear region and scattering from a blood vessel in the ear such that the temporal change in intensity of scattered light is proportional to a temporal change in blood flow within the blood vessel. Another form of optical coupling may be the interaction between excitation light generated by an optical emitter within an earbud and a light-guiding region of the earbud. Thus, an earbud with integrated light-guiding capabilities, wherein light can be guided to multiple and/or select regions along the earbud, can assure that each individual wearing the earbud will generate an optical signal related to blood flow through the blood vessels. Optical coupling of light to a particular ear region of one person may not yield photoplethysmographic signals for each person. Therefore, coupling light to multiple regions may assure that at least one blood-vessel-rich region will be interrogated for each person wearing an earbud. Coupling multiple regions of the ear to light may also be accomplished by diffusing light from a light source within an earbud.

According to some embodiments of the present invention, "smart" monitoring devices including, but not limited to, armbands and earbuds, are provided that change signal analysis frequency and/or sensor module interrogation power in response to detecting a change in subject activity, a change in environmental conditions, a change in time, a change in location of the subject and/or a change in stress level of the subject.

Figure 2B:
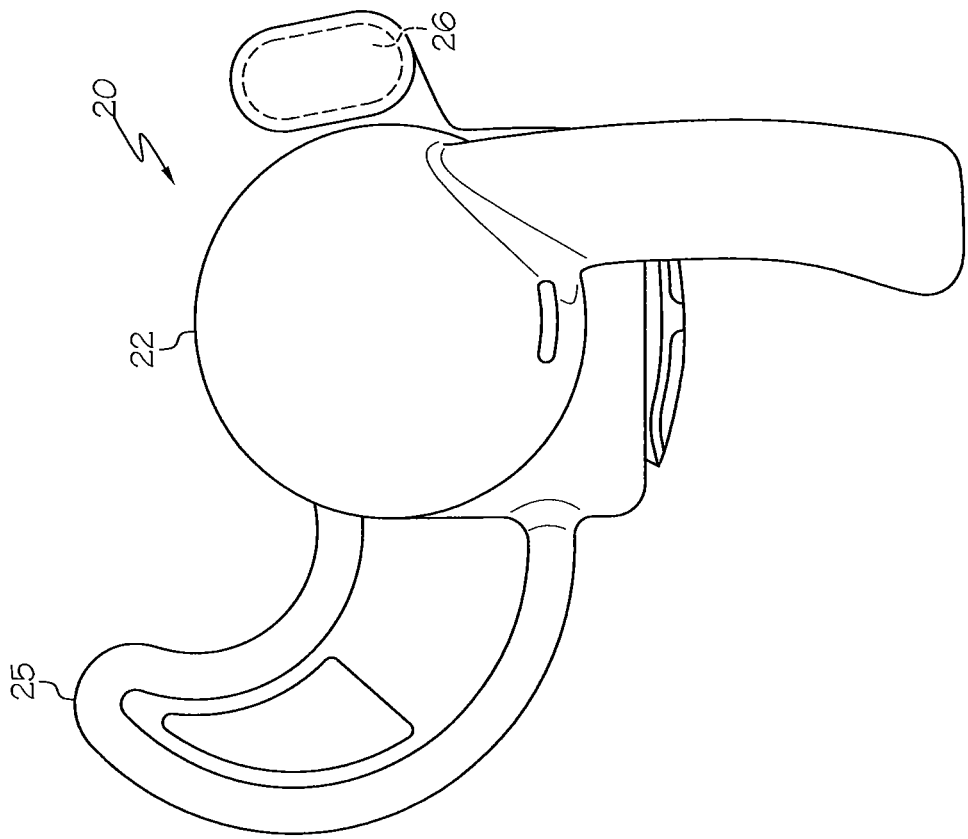
FIGS. 2A-2B illustrate a monitoring device that can be positioned within an ear of a subject, according to some embodiments of the present invention.
Figure 2A:
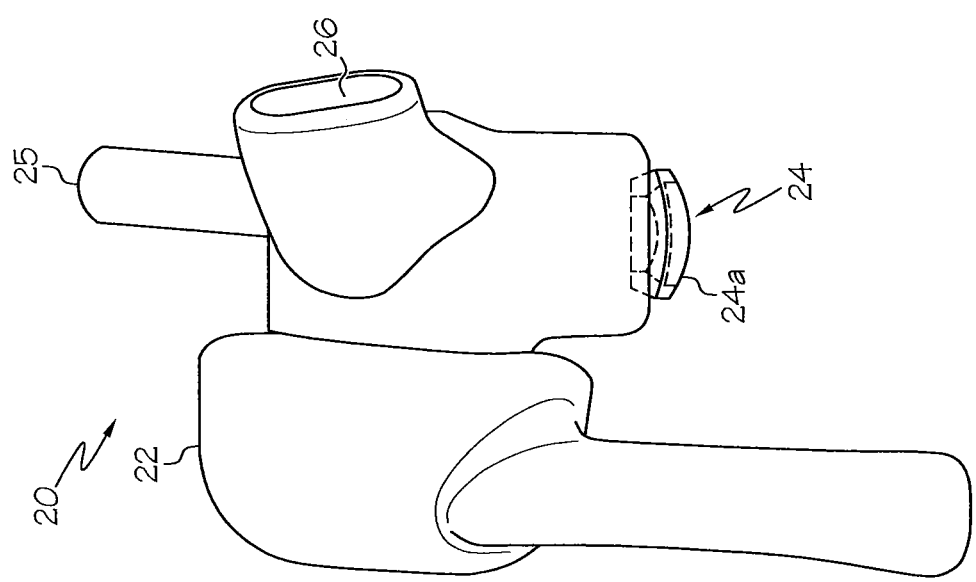

FIGS. 2A-2B illustrate a monitoring apparatus 20 configured to be positioned within an ear of a subject, according to some embodiments of the present invention. The illustrated apparatus 20 includes an earpiece body or housing 22, a sensor module 24, a stabilizer 25, and a sound port 26. When positioned within the ear of a subject, the sensor module 24 has a region 24a configured to contact a selected area of the ear. The illustrated sensor region 24a is contoured (i.e., is "form-fitted") to matingly engage a portion of the ear between the anti tragus and acoustic meatus, and the stabilizer is configured to engage the anti-helix. However, monitoring devices in accordance with embodiments of the present invention can have sensor modules with one or more regions configured to engage various portions of the ear. Various types of device configured to be worn at or near the ear may be utilized in conjunction with embodiments of the present invention.

Figure 3A:
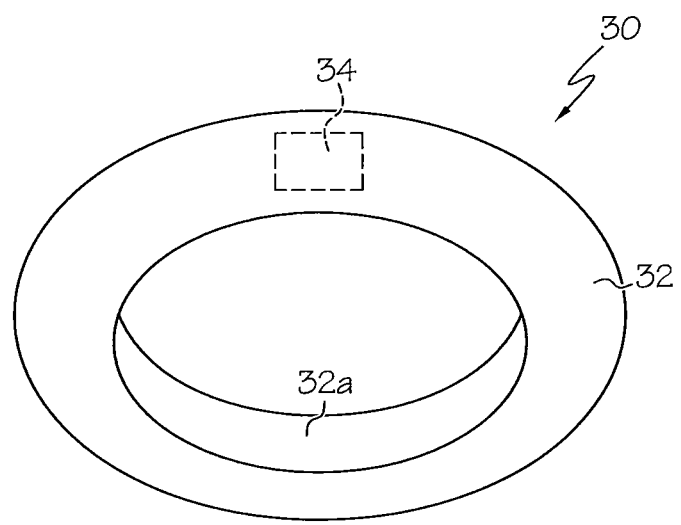
FIG. 3A illustrates a monitoring device that can be positioned around an appendage of the body of a subject, according to some embodiments of the present invention.
Figure 3B:
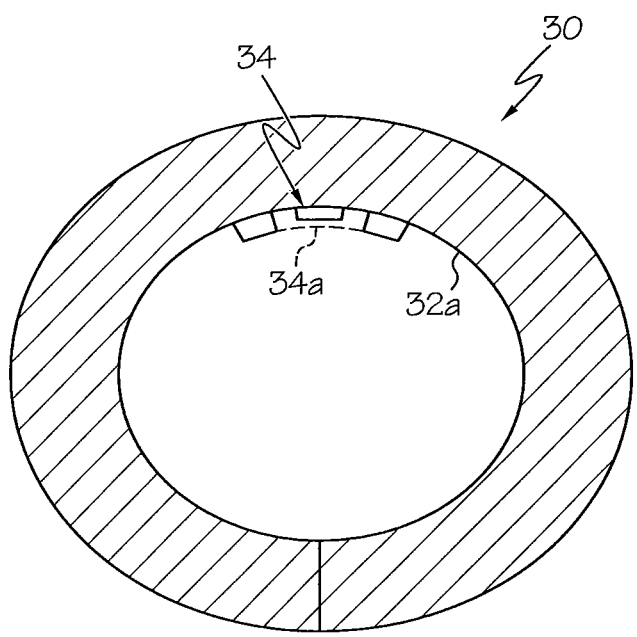
FIG. 3B is a cross sectional view of the monitoring device of FIG. 3A.

FIGS. 3A-3B illustrate a monitoring apparatus 30 in the form of a sensor band 32 configured to be secured to an appendage (e.g., an arm, wrist, hand, finger, toe, leg, foot, neck, etc.) of a subject. The band 32 includes a sensor module 34 on or extending from the inside surface 32a of the band 32. The sensor module 34 is configured to detect and/or measure physiological information from the subject and includes a sensor region 34a that is contoured to contact the skin of a subject wearing the apparatus 30.

Embodiments of the present invention may be utilized in various devices and articles including, but not limited to, patches, clothing, etc. Embodiments of the present invention can be utilized wherever PPG and blood flow signals can be obtained and at any location on the body of a subject. Embodiments of the present invention are not limited to the illustrated monitoring devices 20, 30 of FIGS. 2A-2B and 3A-3B.

The sensor modules 24, 34 for the illustrated monitoring devices 20, 30 of FIGS. 2A-2B and 3A-3B are configured to detect and/or measure physiological information from a subject wearing the monitoring devices 20, 30. In some embodiments, the sensor modules 24, 34 may be configured to detect and/or measure one or more environmental conditions in a vicinity of the subject wearing the monitoring devices 20, 30.

A sensor module utilized in accordance with embodiments of the present invention may be an optical sensor module that includes at least one optical emitter and at least one optical detector. Exemplary optical emitters include, but are not limited to light-emitting diodes (LEDs), laser diodes (LDs), compact incandescent bulbs, micro-plasma emitters, IR blackbody sources, or the like. In addition, a sensor module may include various types of sensors including and/or in addition to optical sensors. For example, a sensor module may include one or more inertial sensors (e.g., an accelerometer, piezoelectric sensor, vibration sensor, photo-reflector sensor, etc.) for detecting changes in motion, one or more thermal sensors (e.g., a thermopile, thermistor, resistor, etc.) for measuring temperature of a part of the body, one or more electrical sensors for measuring changes in electrical conduction, one or more skin humidity sensors, and/or one or more acoustical sensors.

Figure 4:
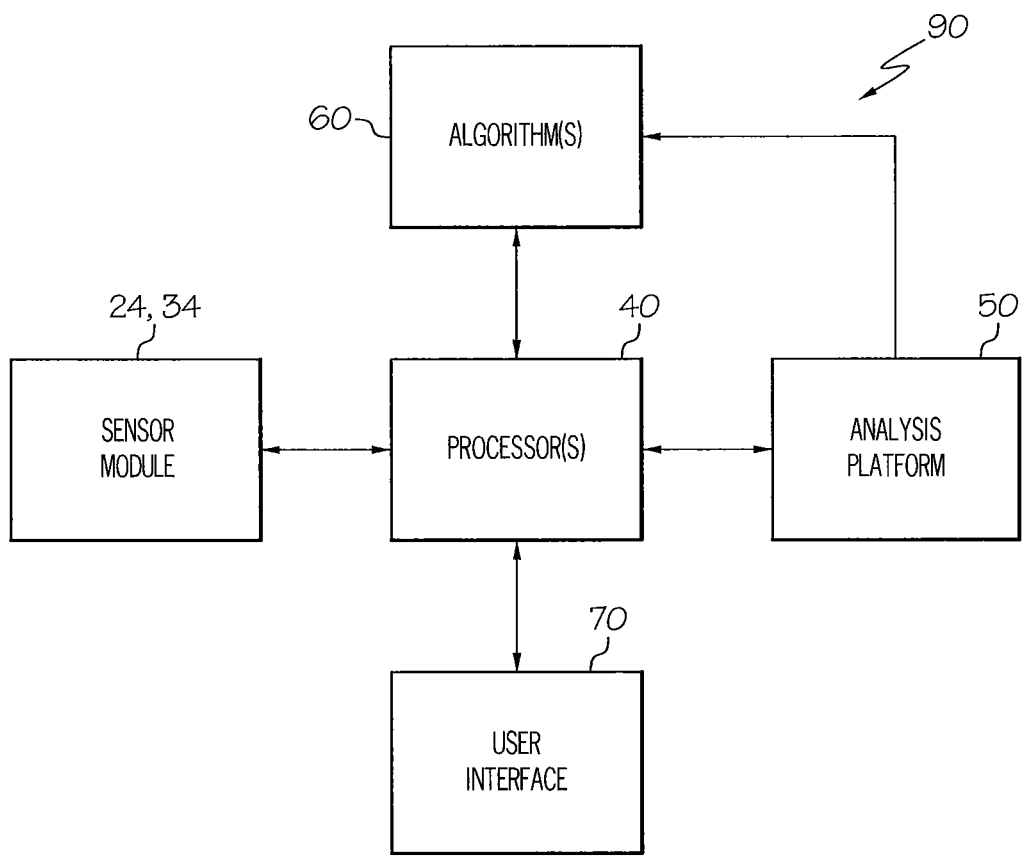
FIG. 4 is a block diagram of a monitoring device according to some embodiments of the present invention.

Referring to FIG. 4, a monitoring device (e.g., monitoring devices 20, 30), according to embodiments of the present invention, includes at least one processor 40 that is coupled to the sensor(s) of a sensor module 24, 34 and that is configured to receive and analyze signals produced by the sensor(s). Collectively, the elements of FIG. 4 present a system for intelligently controlling power consumption in a wearable monitor, such as monitoring devices 20, 30.

The processor 40 is configured to change signal analysis frequency and/or sensor module interrogation power in response to detecting a change in activity of a subject wearing the monitoring device. For example, in some embodiments, the processor 40 increases signal analysis frequency and/or sensor module interrogation power in response to detecting an increase in subject activity, and decreases signal analysis frequency and/or sensor module interrogation power in response to detecting a decrease in subject activity. In other embodiments, the processor 40 implements frequency-domain digital signal processing in response to detecting high subject activity (e.g., the subject starts running, exercising, etc.), and implements time-domain digital signal processing in response to detecting low subject activity. The frequency- and time-domain algorithms represent two different signal extraction methods for extracting accurate biometrics from optical sensor signals, where the frequency-domain algorithm may require substantially greater processing power than that of the time-domain algorithm. The reason that frequency-domain algorithms may require more power is because spectral transforms may be employed, whereas time-domain algorithms may employ lower-power filters and pulse picking.

An analysis platform 50 may be in communication with the processor 40 and a memory storage location 60 for the algorithms. The analysis platform 50 may be within a wearable device (e.g., monitoring devices 20, 30) or may be part of a remote system in wireless or wired communication with the wearable device. The analysis platform 50 may analyze data generated by the processor 40 to generate assessments based on the data. For example, the analysis platform 50 may analyze vital sign data (such as heart rate, respiration rate, RRi, blood pressure, etc.) in context of the user's activity data to assess a health or fitness status of the person, such as a health or fitness score. In a specific example of such an assessment, the analysis platform 50 may assess a subject's $VO_2$max (maximum volume of oxygen consumption) by: 1) identifying data where the subject walked at a speed (as measured by a motion sensor) less than a threshold value (for example, 2.5 mph), 2) selectively analyzing the breathing rate (as measured by a physiological sensor) for this selected data (for example, by taking an average value of the selected breathing rate data and inverting it to get 1/breathing rate), and 3) generating a fitness assessment (such as a $VO_2$max assessment) by multiplying the inverted value by a scalar value. A number of assessments can be made by analyzing physiological and motion (activity) data, and this is only a specific example.

It should be noted that, herein, the steps described wherein the processor 40 is used to make a determination or decision may be interchanged with the analysis platform 50 instead, as the analysis platform may be configured to have the same features as the processor 40 itself. For example, if the processor 40 determines that a subject's $VO_2$max is too high, via an algorithm, the analysis platform 50 may also be configured to assess this determination. Thus, in some embodiments, the analysis platform 50 may be configured such that a processor 40 is not needed, such as the case where a sensor of a sensor module (e.g., sensor module 24, 34) is in wireless communication directly with a remote analysis platform 50.

The analysis platform 50 may be configured to analyze data processed by the processor 40 to assess the efficacy (or confidence value) of the algorithms used by the processor 40 and to autonomously modify the algorithms to improve the acuity of the wearable monitoring device. For example, the processer 40 may be configured to generate a confidence score for a given metric. The confidence score may be an indication of how strongly a processed metric may be trusted. For example, signal-to-noise (S/N) ratio may be processed from a PPG signal by assessing the AC amplitude of the blood flow waveform to a noise value, and a low S/N may represent a low confidence. If the analysis platform 50 determines that confidence value for a given algorithm is low, it may adjust the algorithm for future processing events implemented by the processor 40. For example, the algorithm may be changed such that a threshold may be lowered; as a specific example, the activity threshold for raising the signal analysis frequency and/or sensor module interrogation power may be lowered such that the acuity of the wearable sensor increases during activity. In some embodiments, the analysis platform 50 may determine that an entirely different algorithm must be used for processing, and a replacement algorithm may be selected via command from the analysis platform 50. In some embodiments, this replacement algorithm may be associated with a given confidence value range, and the analysis platform 50 may select the replacement algorithm based on the determined confidence value. For example, if the analysis platform 50 determines that the confidence value of one algorithm is too low for a user, the analysis platform may automatically replace the algorithm with another algorithm that provides higher confidence. However, other methods may be used to select an algorithm for implementation by the processor 40 based on a confidence determination, in accordance with some embodiments of the present invention.

In the case where the sensor module (or modules) comprises PPG sensor functionality, readings from the sensor module (for example, readings from optical sensors or motion sensors) can be used to trigger changes to the optomechanical engine (the optical emitter, detector, and associated optics). For example, the detection of low activity may change the polling of the optomechanical engine. In a specific example, a detection of low activity may change the optical wavelength used for PPG. In this example, if the activity level processed by the processor 40 is deemed to be "low", the primary wavelength of detection may shift from visible (such as green or yellow) wavelengths to infrared wavelengths. This can be useful for automatically turning off visible emitters when the person is rested, helping to prevent visible light pollution so that the person can sleep better.

For example, in one embodiment, the processor 40 and/or analysis platform may determine that the person is sleeping, and then the action of changing wavelengths may be initiated by the processor 40 (i.e., via a command to the PPG sensor). This may be achieved by the processor and/or analytics engine processing activity and/or physiological data against a threshold criteria (i.e., processing accelerometer data to determine a state of low enough physical activity and that the person is laying flat/parallel to the ground) and/or physiological model (i.e., processing PPG sensor information to determine that the person's breathing, heart rate, and/or HRV is of a pattern associated with sleeping) to determine that the person is sleeping. Alternatively, the processor and/or analytics platform may automatically determine that the person is in a dark environment (i.e., by processing optical sensor data to determine that the person is in a dark enough environment) and then send a command to switch change the wavelengths of the PPG sensor. In another embodiment, the user may manually initiate a command (i.e., by pressing a button) that the person is going to sleep, which my then be used by the processor and/or analysis platform to change the wavelengths. Also, although the PPG S/N ratio for infrared (IR) wavelengths may be less than that for visible wavelengths, the total electrical power levels (i.e., the bias voltage) required to bias the IR emitter may be lower, thereby saving battery life in conditions of low activity.

This approach may also be used for pulse oximetry via a PPG sensor. For example, the processor 40 may process sensor readings from a sensor module 24, 34 to determine that the subject wearing the wearable device is indoors or outdoors, and the processor 40 may select a different optomechanical polling routine for indoors vs. outdoors. For example, when indoors, a visible and IR emitter may be engaged to facilitate $SpO_2$ determination. But once the user is outdoors, where visible outdoor light may pollute PPG sensor readings with noise signals too intense to remove with physical or digital optical filters, the processor may engage (poll) multiple IR emitters instead of the visible and IR emitter, and $SpO_2$ determination may be executed via two IR wavelength bands rather than a visible+IR wavelength band. For example, the processor 40 may turn off visible emitters when the user is outdoors and may turn on multiple IR emitters, such as a ~700 nm and ~940 nm emitter, instead. Because pulse oximetry requires two distinct wavelengths or two different wavelength bands in order to generate an estimate of SpO2, these two IR wavelengths/wavelength bands may be used with efficacy outdoors. The example of these two wavelengths/wavelength bands should not be construed to be limiting, as various wavelength configurations more resilient to outdoor light contamination may be used, such as spectral bands in solar blind regions (wavelengths that are naturally attenuated by the earth's atmosphere, such as ~763 nm and others). Additionally, it should be noted that monitoring blood oxygen (SpO2) and tissue oxygen may each be achieved via this method, depending on the sensor positioning used. For example, locating a PPG sensor at a leg or arm may facilitate a more accurate determination of muscle oxygenation, whereas locating a PPG sensor at a finger, ear, or forehead may be facilitate a more accurate determination of blood oxygenation. Moreover, the muscle oxygenation signals collected may be used as a proxy for estimating lactic acid and/or lactate threshold (or anaerobic threshold) in the muscle of the subject, as oxygen depletion may be correlated with higher lactic acid build-up in the muscles.

Besides the example just described, autonomously triggering changes in the optomechanical engine of a PPG sensor, in response to activity data sensed by an activity (motion) sensor, can be applied towards a number of useful functions. For example, the detection of low activity may change the type of PPG-based measurement to be executed. This can be useful for cases where the accuracy of a physiological measurement or assessment demands a certain level of physical activity or inactivity. As a specific example, a measurement of blood pressure or RRi (R-R interval, which is the interval from the peak of one QRS complex to the peak of the next as shown on an electrocardiogram) may provide best results during periods of inactivity. The processor 40 may deem that activity is "low enough" to execute one or more of such measurements, and then execute an algorithm to start measuring. This way, blood pressure and/or RRi measurements are only executed at time periods where a reliable measurement can be made, thereby saving system power. Similarly, in some embodiments, a measurement of HRR (heart rate recovery) may be executed only when the processor 40 deems that activity "high enough" to make such a measurement meaningful. For example, the processor 40 may determine that a user's activity level (perhaps as sensed by an activity sensor) or exertion level (perhaps as sensed by a heart rate sensor) has been high enough for a long enough period of time, followed by a resting phase, such that HRR may be accurately assessed. In this case, several data points of activity level and/or heart rate may be stored in memory or buffered, such that the processor 40 may run through the dataset to determine if the user has been in a state of high activity or exertion for a long enough period of time to justify an HRR measurement. This way, HRR measurements are only executed at time periods where a reliable measurement can be made, saving power consumption.

In another example, if the processor 40 determines that subject activity level has been very low, the processor 40 may engage a longer wavelength light, such as IR light, as the wavelength for PPG. But if subject activity is heightened, the processor 40 may switch the wavelength to a shorter wavelength, such as green, blue, or violet light. Such a process may address the problem of low perfusion, which often prevents PPG readings during periods of subject inactivity, especially for wrist-based PPG sensors. Shorter wavelength light for PPG generally yields a higher signal-to-noise ratio (S/N) over longer wavelength, but low perfusion can reduce blood flow at the surface of the skin, pushing blood flow so far below the surface that shorter wavelength light is absorbed by the skin before reaching blood flow. However, during exercise, perfusion may return and shorter wavelength light may be used once again, providing a higher S/N for PPG and thereby reducing system power requirements.

In another example, if the processor 40 determines that subject perfusion is low, for example by processing PPG information to determine that the signal-to-noise level is quite low, the processor 40 may send a command to the sensor module 24, 34 to raise the localized temperature of the neighboring skin, thereby increasing perfusion. This may be achieved by the processor 40 sending a command to turn on a heater element on the sensor module 24, 34 or to increase the electrical bias across an LED such that the LED heats up the skin to encourage blood flow. Once the signal-to-noise level is determined to be high enough for accurate and reliable physiological monitoring by the processor 40, the processor 40 may send a command to terminate heating of the skin. For the case of PPG sensor modules 24, 34 in the system of FIG. 4, there are certain wavelengths of light that may be better for sensing specific biometric parameters. For example, whereas IR or green light may be best for sensing heart rate-related modulations in blood flow, blue or violet light may be best for sensing respiration-related modulations in blood flow. Thus, in some embodiments of the present invention, the processor 40 may be configured to select a given PPG wavelength routinely in time, according to an algorithm 60, such that various parameters are measured sequentially in time order rather than being measured simultaneously in a continuous fashion. In this way, various wavelengths of light can be turned on and off at different periods in time in order to measure various biometric parameters in sequence.

Readings from sensor module(s) can also be used to trigger a change in the algorithm sequence executed by a processor 40. For example if a normal heart rate level and/or heart rate variability (HRV) level is detected by the processor (such as a heart rate and/or HRV within a specified range), then the processor 40 may select an algorithm that has less sequential steps in time, thus saving power on the processor 40. More specifically, once an abnormal heart rate and/or HRV is detected outside the specified range, the processor 40 may select an algorithm that also implements continuous cardiac monitoring, such as monitoring of arrhythmia, atrial fibrillation, blood pressure, cardiac output, irregular heart beats, etc. And when heart rate and/or HRV fall back within the specified range, the processor 40 may return to a lower-power algorithm with less sequential steps in time.

Readings from the sensor(s) of a monitoring device can be used to trigger events. In addition, sensor signals may be processed and algorithms may be selected to control a biometric signal extraction method. For example, elevated subject physical activity sensed by an accelerometer may trigger a change in the signal extraction algorithm for PPG towards one of higher acuity (but higher power usage); then, when subject activity winds down, the algorithm may change to one that is lower acuity (but lower power usage). In this way, battery power may be preserved for use cases where high acuity is not needed (such as sedentary behavior where motion artifacts need not be removed.)

In some embodiments, detecting a change in subject activity comprises detecting a change in at least one subject vital sign, such as subject heart rate, subject blood pressure, subject temperature, subject respiration rate, subject perspiration rate, etc. In other embodiments, the sensor module includes a motion sensor, such as an accelerometer, gyroscope, etc., and detecting a change in subject activity includes detecting a change in subject motion via the motion sensor.

According to some embodiments, the type of activity may be identified or predicted via the processor 40. Changing signal analysis frequency and/or sensor module interrogation power may be based on stored profiles (such as a look-up table) or learned profiles (such as machine learning with human input) of activity identification information, such as: 1) a known accelerometry profile for a given sport or exercising activity and/or 2) a known accelerometry profile for a particular person, for example.

According to other embodiments of the present invention, a monitoring device configured to be attached to a subject, such as monitoring devices 20, 30, includes a sensor module configured to detect and/or measure physiological information from the subject and to detect and/or measure at least one environmental condition in a vicinity of the subject. The sensor module may be an optical sensor module that includes at least one optical emitter and at least one optical detector, although various other types of sensors may be utilized. A processor 40 is coupled to the sensor module and is configured to receive and analyze signals produced by the sensor module. In addition, the processor 40 is configured to change signal analysis frequency and/or sensor module interrogation power in response to detecting a change in the at least one environmental condition. Exemplary changes in environmental conditions include changes in one or more of the following ambient conditions: temperature, humidity, air quality, barometric pressure, radiation, light intensity, and sound. In some embodiments, the processor 40 increases signal analysis frequency and/or sensor module interrogation power in response to detecting an increase in the at least one environmental condition, and decreases signal analysis frequency and/or sensor module interrogation power in response to detecting a decrease in the at least one environmental condition. For example, the signal analysis frequency and/or sensor module interrogation power may be increased when air quality worsens or becomes detrimental to the wearer, and signal analysis frequency and/or sensor module interrogation power may be decreased when air quality improves. The principle behind this process is that extreme or harsh ambient changes in environment (such as extreme hot or cold, extreme humidity or dryness, etc.) may lower the S/N ratio of the processed signals. Thus, higher processing power may be required to actively remove noise.

Figure 5:
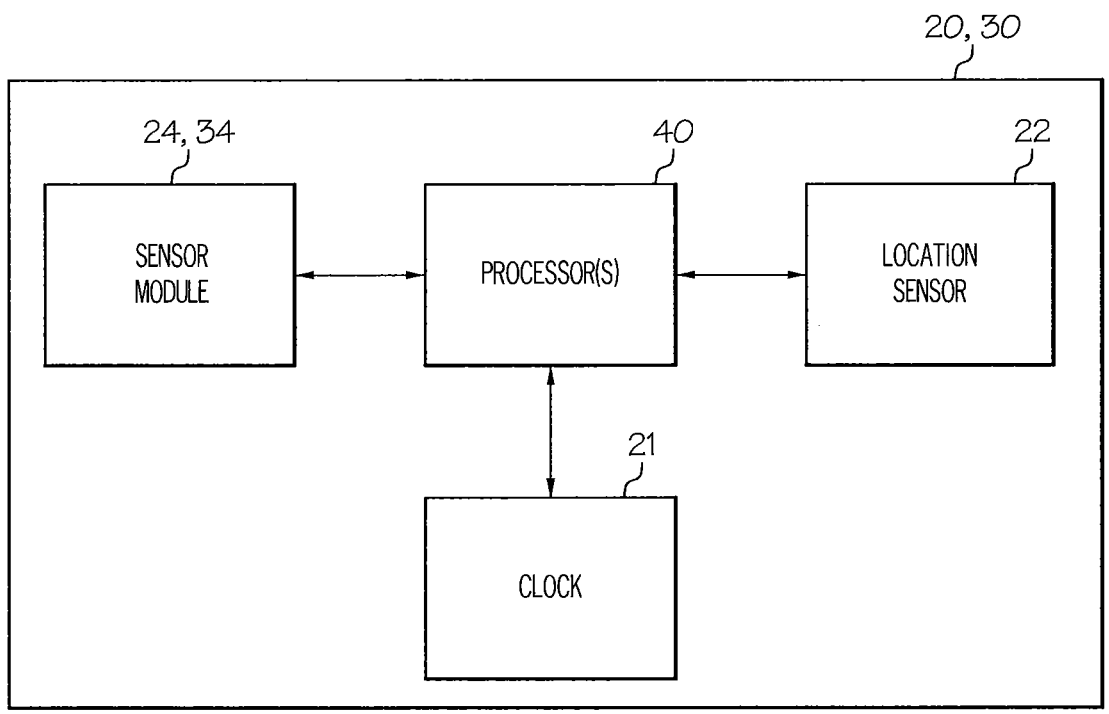
FIG. 5 is a block diagram of a monitoring device according to some embodiments of the present invention.

Referring to FIG. 5, according to other embodiments of the present invention, a monitoring device configured to be attached to a subject, such as monitoring devices 20, 30, includes a clock 82 (or is in communication with a clock 82), a sensor module 24, 34 configured to detect and/or measure physiological information from the subject (and/or environmental condition information in a vicinity of the subject), and a processor 40 coupled to the clock 82 and the sensor module. The sensor module 24, 34 may be an optical sensor module that includes at least one optical emitter and at least one optical detector, although various other types of sensors may be utilized. The processor 40 is configured to receive and analyze signals produced by the sensor module 24, 34, and is configured to change signal analysis frequency and/or changes sensor module interrogation power at one or more predetermined times.

In some embodiments, the processor 40 increases signal analysis frequency and/or sensor module interrogation power at a first time, and decreases signal analysis frequency and/or sensor module interrogation power at a second time. For example, signal analysis frequency and/or sensor module interrogation power may be increased at a particular time of day (e.g., the time of day when the wearer is typically exercising), and may be decreased at another time of day, for example, at a time of day when the wearer is less active (e.g., nighttime, etc.).

In other embodiments, the processor 40 adjusts signal analysis frequency and/or sensor module interrogation power according to a circadian rhythm of the subject. For example, signal analysis frequency and/or sensor module interrogation power may be increased at a particular time of day (e.g., the time of day when the wearer is at peak metabolism), and may be decreased at another time of day (for example, during sleep).

In other embodiments, the processor 40 adjusts signal analysis frequency and/or interrogation power of a sensor module 24, 34 or analysis platform 50 based on the determined stress state of the user. For example, the processor 40 may determine that a user is psychologically stressed based on, for example, an elevated heart rate over a period of time during low (not high) physical activity. The processor 40 may then send a signal to another sensor and/or analysis platform, such as a voice analysis/recognition system 84 that is in communication with the system 90 of FIG. 4, to control the processing power of voice recognition. In this manner, a more stressed psychological state may result in a higher processing power for the voice recognition system 84; in contrast, a low stress state may trigger lower power processing because it may be easier for the voice recognition system 84 to understand someone when they are calm rather than excited. As another example, the processor 40 may identify a pattern of low heart rate by processing information from a heart rate sensor over a period of time; in response, the processor may lower the signal analysis frequency and/or interrogation power performed in another simultaneous measurement, such as RRi (R-R interval). Though the sampling frequency may be reduced for the RRi calculation in this example, RRi acuity may not be sacrificed because lower heart rate implies generally longer R-R intervals. Longer intervals do not require high sampling rates for detection/measurement.

As yet another example, the processor 40 may adjust signal analysis frequency and/or interrogation power of a user interface 70 that is in communication with the system 90 of FIG. 4 (e.g., a user interface of a telecommunication device, such as a smartphone, computer, etc., or a user interface associated with a monitoring device 20, 30), based on the determined stress state of a subject wearing a monitoring device 20, 30. In this example, the processor 40 may determine that a user is psychologically stressed and then send a signal (i.e., a command) to the user interface 70, such as a view screen, such that the font size of displayed text is increased and/or the screen brightness is increased and/or an image displayed within the user interface 70 is easier to view/comprehend (e.g., increase the resolution of the image, etc.). Then, once the processor 40 determines that the subject's stress level is sufficiently low, the processor 40 may signal a low-power mode of operation for the user interface 70, by lowering the screen brightness and/font size of displayed text and/or reducing the resolution of a displayed image(s), for example.

According to other embodiments of the present invention, a monitoring device configured to be attached to a subject, such as monitoring devices 20, 30, includes a location sensor 80 (FIG. 5), a sensor module 24, 34 configured to detect and/or measure physiological information from the subject, and a processor 40 coupled to the location sensor 80 and the sensor module 24, 34. The sensor module 24, 34 may be an optical sensor module that includes at least one optical emitter and at least one optical detector, although various other types of sensors may be utilized. The processor 40 is configured to receive and analyze signals produced by the sensor module 24, 34 and to change signal analysis frequency and/or sensor module interrogation power when the location sensor 80 indicates the subject has changed locations.

In some embodiments, the processor 40 increases signal analysis frequency and/or sensor module interrogation power when the location sensor 80 indicates the subject is at a particular location, and decreases signal analysis frequency and/or sensor module interrogation power when the location sensor 80 indicates the subject is no longer at the particular location. For example, signal analysis frequency and/or sensor module interrogation power may be increased when the location sensor 80 indicates the subject is at a particular location (e.g., at the gym, outdoors, at the mall, etc.), and may be decreased when the location sensor 80 indicates the subject is no longer at the particular location (e.g., when the wearer is at work, home, etc.). The locations selected for the increase or decrease in processing power may be personalized for the user and stored in memory. For example, people who are more active at outdoors than at work may see the decision tree described above, but for those who are more active at work, the decision tree may be swapped such that higher power processing is selected for work locations over home locations.

Other factors may be utilized to trigger an increase or decrease in signal analysis frequency and/or sensor module interrogation power. For example, higher body temperature readings detected by a thermal sensor associated with the sensor module 24, 34 may trigger changes in signal analysis frequency and/or sensor module interrogation power. The principle behind this may be that higher body temperatures are associated with higher motion, for example. The detection of higher light levels, the detection of higher changes in light intensity, and/or the detection of particular wavelengths via an optical sensor associated with the sensor module 24, 34 may trigger changes in signal analysis frequency and/or sensor module interrogation power. Lower potential drops detected by an electrical sensor associated with the sensor module 24, 34 may trigger changes in signal analysis frequency and/or sensor module interrogation power. Lower skin humidity readings detected via a humidity sensor associated with the sensor module may trigger changes in signal analysis frequency and/or sensor module interrogation power. Higher acoustic noise levels detected via an acoustical sensor associated with the sensor module 24, 34 may trigger changes in signal analysis frequency and/or sensor module interrogation power.

Figure 6:
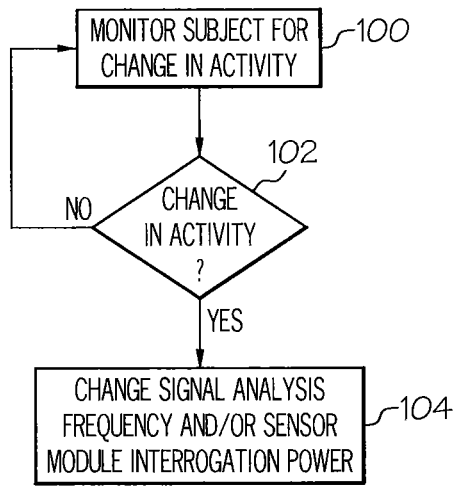
FIGS. 6, 7A-7B, and 8-20 are flowcharts of operations for monitoring a subject according to embodiments of the present invention.

Referring now to FIG. 6, a method of monitoring a subject via a monitoring device, such as monitoring devices 20, 30, according to some embodiments of the present invention, will be described. The monitoring device includes a sensor module 24, 34 configured to detect and/or measure physiological information from the subject and a processor 40 configured to receive and analyze signals produced by the sensor module. The subject is monitored for change in physical activity level (Block 100). If a change is detected (Block 102), the processor 40 changes signal analysis frequency and/or sensor module interrogation power (Block 104).

Figure 7A:
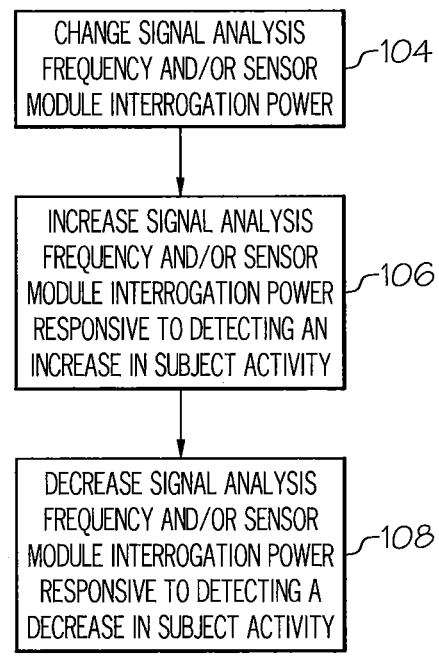

As illustrated in FIG. 7A, changing signal analysis frequency and/or sensor module interrogation power (Block 104) may include increasing signal analysis frequency and/or sensor module interrogation power in response to detecting an increase in subject activity (Block 106), and decreasing signal analysis frequency and/or sensor module interrogation power in response to detecting a decrease in subject activity (Block 108). As described above, one method of lowering the interrogation power is powering only one electrode, or powering less electrodes, in a sensor module 24, 34 or sensor element such that less total interrogation power is exposed to the body of a subject. For example, in response to detecting an increase in subject activity (Block 106), the system of FIG. 4 may power only one optical emitter (or illuminate less optical emitters) in the sensor module 24, 34, rather than a plurality of optical emitters that may be present in a wearable PPG module. Then, once high activity is detected, for example high activity detected during exercise, the system may return power to all of the optical emitters (or more of the optical emitters) in the PPG module. Because low activity may require less light for accurate PPG monitoring when compared with high physical activity, in the described manner, both high and low activity levels can result in accurate PPG measurements while balancing power requirements.

Figure 7B:
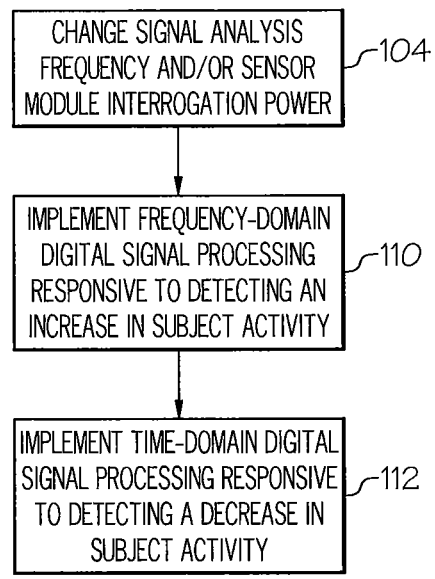

In other embodiments as illustrated in FIG. 7B, changing signal analysis frequency and/or sensor module interrogation power (Block 104) may include implementing frequency-domain digital signal processing in response to detecting an increase in subject activity (Block 110), and implementing time-domain digital signal processing in response to detecting a decrease in subject activity (Block 112).

Figure 8:
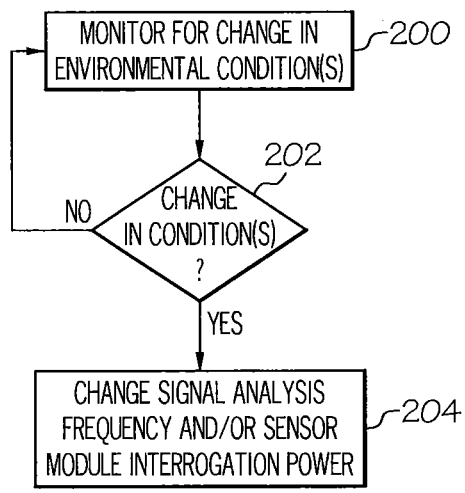
Figure 9:
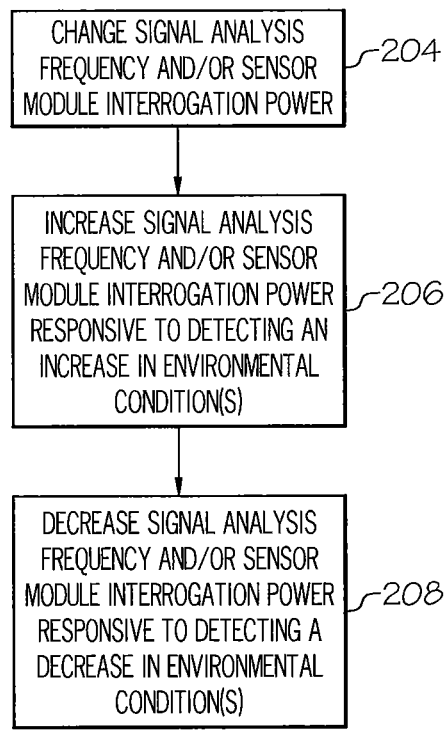

Referring now to FIG. 8, a method of monitoring a subject via a monitoring device, such as monitoring devices 20, 30, according to some embodiments of the present invention, will be described. The monitoring device includes a sensor module 24, 34 configured to detect and/or measure physiological information from the subject and/or measure at least one environmental condition in a vicinity of the subject, and a processor 40 coupled to the sensor module 24, 34 that is configured to receive and analyze signals produced by the sensor module 24, 34. The vicinity of the subject is monitored for changes in one or more environmental conditions (Block 200). If a change is detected (Block 202), the processor 40 changes signal analysis frequency and/or sensor module interrogation power (Block 204). As illustrated in FIG. 9, changing signal analysis frequency and/or sensor module interrogation power (Block 204) may include increasing signal analysis frequency and/or sensor module interrogation power in response to detecting an increase in an environmental condition (e.g., an increase in temperature, humidity, air pollution, light intensity, sound, etc.) (Block 206), and decreasing signal analysis frequency and/or sensor module interrogation power in response to detecting a decrease in an environmental condition (e.g., a decrease in temperature, humidity, air pollution, light intensity, sound, etc.) (Block 208).

Figure 10:
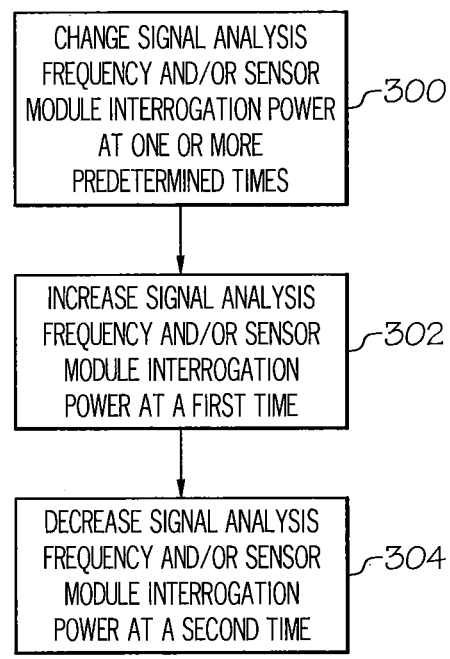
Figure 11:
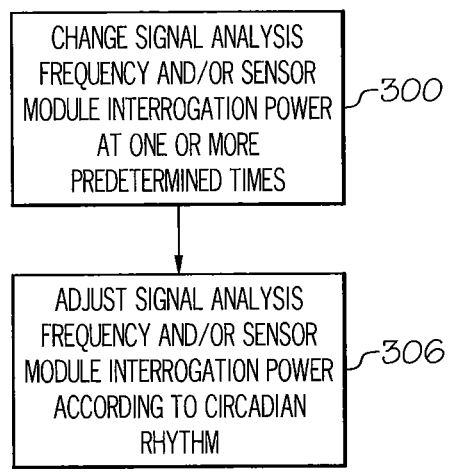

Referring now to FIG. 10, a method of monitoring a subject via a monitoring device, such as monitoring devices 20, 30, according to some embodiments of the present invention, will be described. The monitoring device includes or is in communication with a clock 82, a sensor module 24, 34 configured to detect and/or measure physiological information from the subject, and a processor 40 coupled to the clock 82 and the sensor module 24, 34 that is configured to receive and analyze signals produced by the sensor module 24, 34. The processor 40 changes signal analysis frequency and/or sensor module interrogation power at one or more predetermined times (Block 300). For example, signal analysis frequency and/or sensor module interrogation power is increased at a first time (e.g., at a particular time of the day, week, etc.) (Block 302) and signal analysis frequency and/or sensor module interrogation power is decreased at a second time (e.g., another time of the day, week, etc.) (Block 304). In other embodiments, as illustrated in FIG. 11, changing signal analysis frequency and/or sensor module interrogation power at one or more predetermined times (Block 300) includes adjusting signal analysis frequency and/or sensor module interrogation power according to a circadian rhythm of the subject (Block 306).

Figure 12:
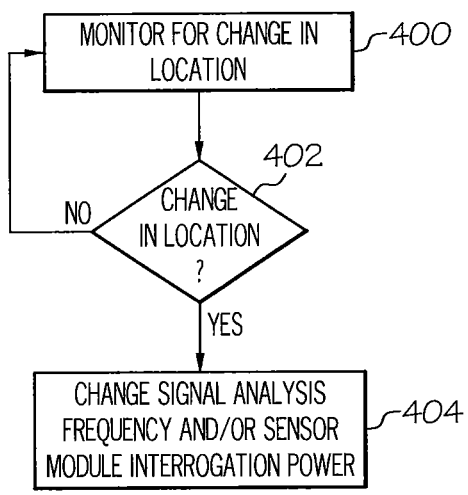
Figure 13:
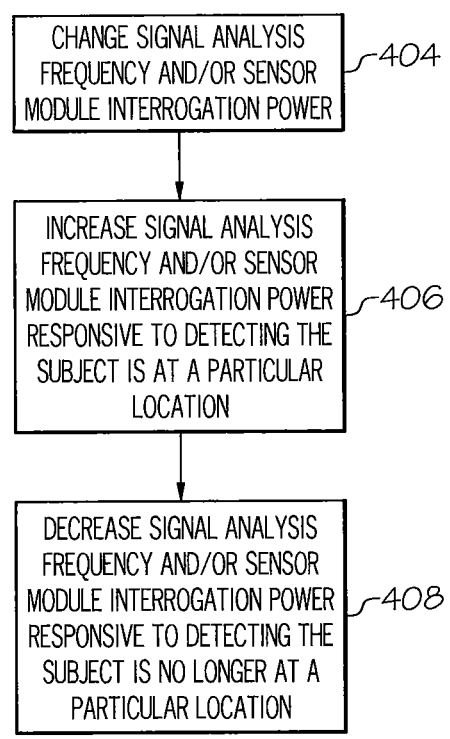

Referring now to FIG. 12, a method of monitoring a subject via a monitoring device, such as monitoring devices 20, 30, according to some embodiments of the present invention, will be described. The monitoring device includes a location sensor 80 (or is in communication with a location sensor 80), a sensor module 24, 34 configured to detect and/or measure physiological information from the subject, and a processor 40 coupled to the location sensor 80 and the sensor module 24, 34 that is configured to receive and analyze signals produced by the sensor module 24, 34. The subject is monitored for a change in location (Block 400). If a change is detected (Block 402), the processor 40 changes signal analysis frequency and/or sensor module interrogation power (Block 204). As illustrated in FIG. 13, changing signal analysis frequency and/or sensor module interrogation power (Block 404) may include increasing signal analysis frequency and/or sensor module interrogation power in response to detecting that the subject is at a particular location (Block 406), and decreasing signal analysis frequency and/or sensor module interrogation power in response to detecting that the subject is no longer at the particular location (Block 408). For example, signal analysis frequency and/or sensor module interrogation power may be increased when it is detected that the subject is at the gym and signal analysis frequency and/or sensor module interrogation power may be decreased when it is detected that the subject has returned home.

Figure 14:
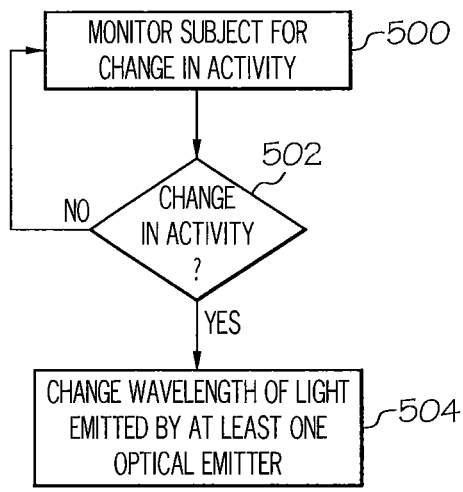

Referring now to FIG. 14, a method of monitoring a subject via a monitoring device, such as monitoring devices 20, 30, according to some embodiments of the present invention, will be described. The monitoring device includes a sensor module 24, 34 configured to detect and/or measure physiological information from the subject and a processor configured to receive and analyze signals produced by the sensor module 24, 34. The sensor module 24, 34 includes at least one optical emitter and at least one optical detector. The subject is monitored for change in physical activity level (Block 500). If a change is detected (Block 502), the processor 40 changes wavelength of light emitted by the at least one optical emitter (Block 504).

Figure 15:
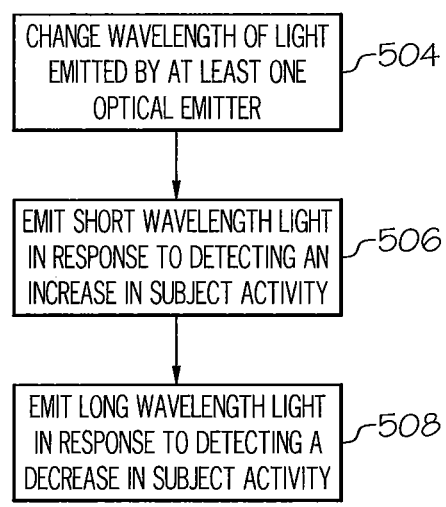

As illustrated in FIG. 15, changing wavelength of light emitted by the at least one optical emitter (Block 504) may include emitting shorter wavelength light in response to detecting an increase in subject activity (Block 506), and emitting longer wavelength light in response to detecting an decrease in subject activity (Block 508). Shorter wavelength light may be less susceptible to motion artifacts. Longer wavelength light may require less battery power and also may be invisible to the eye and thus more appealing for long-term wear of a wearable monitor.

Figure 16:
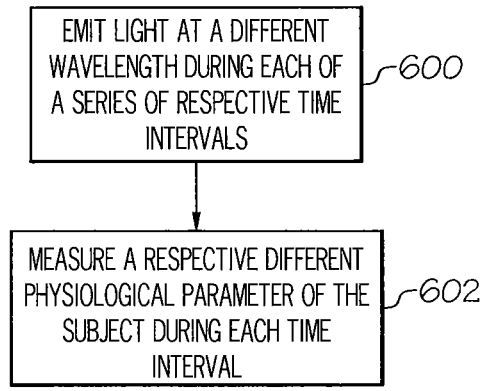

Referring now to FIG. 16, a method of monitoring a subject via a monitoring device, such as monitoring devices 20, 30, according to some embodiments of the present invention, will be described. The monitoring device includes a sensor module 24, 34 configured to detect and/or measure physiological information from the subject and a processor 40 configured to receive and analyze signals produced by the sensor module 24, 34. The sensor module 24, 34 includes at least one optical emitter and at least one optical detector. The sensor module 24, 34 emits light, via the at least one optical emitter, at one or more wavelengths during each of a series of respective time intervals (Block 600) to facilitate the measurement of a variety of different physiological parameters of the subject in the respective time intervals via data collected by the at least one optical detector (Block 602).

For example, an algorithm may comprise a list of successive intervals, wherein each interval may comprise: 1) a different polling of the optical emitter and/or detector and/or 2) a different interrogation wavelength or set of interrogation wavelengths. As a specific example, an algorithm may focus on collecting and/or processing information for the measurement of heart rate, RRi, and blood pressure in order. In such case, the following intervals may be executed in series (in no particular order): 1) calculate heart rate, 2) calculate RRi, 3) calculate blood pressure, and 4) calculate breathing rate. Heart rate may be calculated with a processor-intensive calculation to actively remove motion artifacts via a motion (noise) reference, such as footstep and body motion artifacts, as disclosed in U.S. Patent Application Publication No. 2015/0018636, U.S. Patent Application Publication No. 2015/0011898, U.S. Pat. No. 8,700,11, and U.S. Pat. No. 8,157,730, which are incorporated herein by reference in their entireties.

RRi may be calculated via a time-domain approach, such as applying a processor-efficient peak-finder or by leveraging a heart rate feedback filter to improve RRi tracking, for example as disclosed in U.S. Patent Application Publication No. 2014/0114147, which is incorporated herein by reference in its entirety. Blood pressure may be calculated by processing the photoplethysmogram itself (e.g., via intensity, shape, 1st derivative, 2nd derivative, integral, etc.) via a processor-efficient time-domain algorithm. Breathing rate (respiration rate) may be calculated by running the optical detector signal through a low-pass filter, in some cases by applying a variable feedback loop to align the corner frequency with the heart rate, for example as disclosed in U.S. Patent Application Publication No. 2014/0114147.

In all four cases of this specific example, a different optical wavelength (or a different set of wavelengths) may be used. For example, calculating heart rate may employ a variety of different wavelengths, but calculating breathing rate may employ shorter-wavelength light (such as wavelengths shorter than 600 nm, or preferably shorter than 480 nm) such that heart rate PPG signals do not overpower breathing rate PPG signals during processing of breathing rate. In the example just given, with 4-intervals of optical signal sampling, further power reductions can be realized by an algorithm which selects which intervals to execute depending on the activity state of the user. For example, if the activity state reaches a certain threshold, the algorithm may select that only the first and fourth intervals (the heart rate and breathing rate data collection intervals) are activated. Similarly, if the activity state is below a certain threshold, the algorithm may select that only the second and third intervals (the RRi and blood pressure intervals) are activated. In this manner, only the physiological parameters that are relevant to a particular activity state may be calculated, thereby saving system power and increasing the battery life of the wearable monitoring device.

In some embodiments, the wavelength of the optical emitter and optical detector may stay the same for each interval, but in contrast the sampling and/or polling of the sensor element (i.e., the sampling of the detector(s) and the polling of the emitter(s)) may be changed depending on the measurement goal of each interval. For example, an algorithm may focus on processing at least one photoplethysmogram to measure or estimate 1) blood pressure (highest sampling and/or polling), 2) heart rate variability (2nd-higest sampling and/or polling), and 3) low-motion ("lifestyle") heart rate monitoring (lowest sampling and/or polling) in sequence. This may be because accurately assessing blood pressure from a photoplethysmogram may require a higher data acuity, whereas accurate heart rate variability may require less acuity, and heart rate under lifestyle (low motion) conditions may require the least acuity. In another embodiment, the polling and/or sampling for blood pressure may be greater than 125 Hz, the polling and/or sampling of HRV may be between 250 Hz and 100 Hz, and the polling and/or sampling of lifestyle heart rate may be less than 75 Hz.

In another embodiment, an algorithm may focus on processing at least one photoplethysmogram to generate a single real-time biometric parameter at different intervals, with each interval having a different polling and/or sampling rate. As an example, an algorithm may process a photoplethysmogram to generate RRi at various different intervals where, for each interval, the polling rate of the optical emitter and the sampling rate of the optical detector may be different. As a specific example, there may be three intervals, each having an increasingly lower polling and/or sampling rate. The optimum sampling rate to maintain measurement accuracy while limiting power consumption has been found by experiment, as shown in FIGS. 21A and 21B.

Figures 21A, 21B:
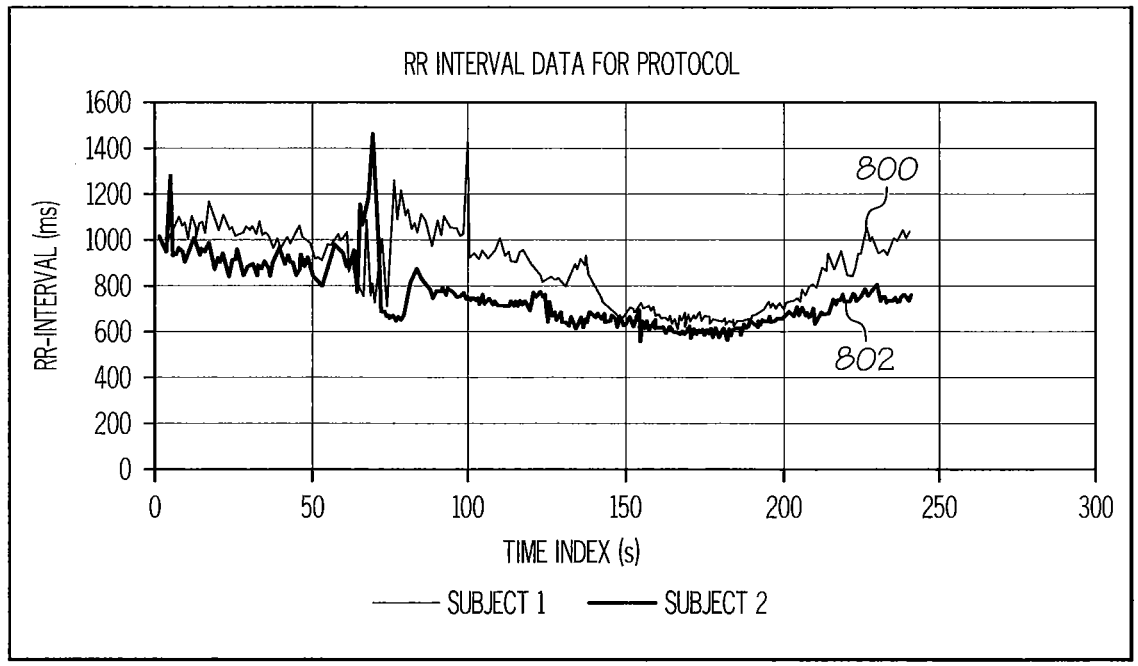
FIG. 21A is a graph illustrating two plots of real-time RRi (R-R interval) measurements taken from two different subjects wearing a PPG sensor during a period of 240 seconds: 60 seconds sitting in a chair, 60 seconds standing in place, 60 seconds fast walking, and 60 seconds of easy walking.
FIG. 21B is a table which illustrates various calculated statistical metrics for the plots of the two subjects of FIG. 21A at three different polling and sampling frequencies (250 Hz, 125 Hz, and 25 Hz).

FIG. 21A presents two plots 800, 802 of real-time RRi measurements taken from two different subjects wearing a PPG sensor (e.g., monitoring devices 20, 30) during a period of 240 seconds: 60 seconds sitting in a chair, 60 seconds standing in place, 60 seconds fast walking, and 60 seconds of easy walking. Plot 800 is of subject one and plot 802 is of subject two. Post analysis of these two datasets yields the table 810 shown in FIG. 21B, which illustrates various calculated statistical metrics for the plots of subject one and subject two at three different polling and sampling frequencies (250 Hz, 125 Hz, and 25 Hz). It can be seen that the calculated median and mean values of RRi is nearly identical for all of the frequencies for each respective subject. However, the calculated values for SD (standard deviation) and NN50 (the number of pairs of successive R-R intervals, "NNs", that differ by greater than 50 milliseconds) are shown to be dependent on sampling frequency. Thus, from FIG. 21B, in order to maintain measurement accuracy while keeping power consumption low, it can be shown that an ideal polling/sampling for the proposed three intervals may be ~125 Hz for the NN50 calculation, between 125 and 25 Hz for the SD calculation, and 25 Hz for a heart rate calculation during low physical activity (lifestyle conditions).

Figure 17:
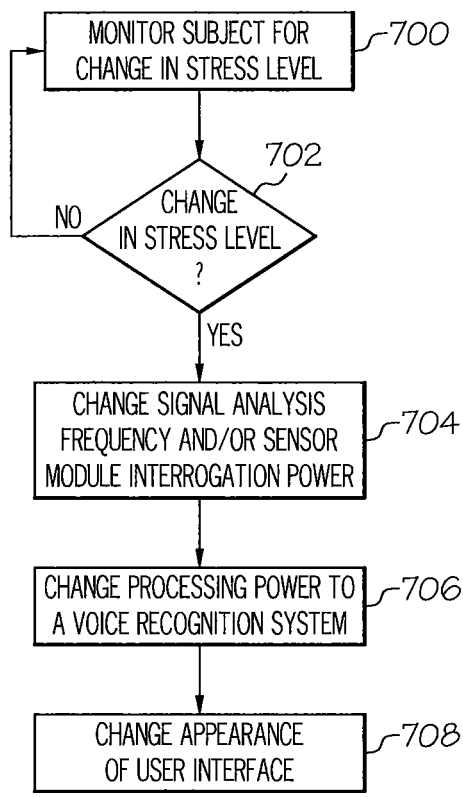

Referring now to FIG. 17, a method of monitoring a subject via a monitoring device, such as monitoring devices 20, 30, according to some embodiments of the present invention, will be described. The monitoring device includes a sensor module 24, 34 configured to detect and/or measure physiological information from the subject and a processor 40 configured to receive and analyze signals produced by the sensor module 24, 34. The subject is monitored for change in stress level (Block 700). If a change is detected (Block 702), the processor 40 changes signal analysis frequency and/or sensor module interrogation power (Block 704). In some embodiments, if a change is detected, the measurement intervals (as described previously) may change. In some embodiments, if a change is detected (Block 702), processing power to a voice recognition system 84 associated with the monitoring device is changed (Block 706). In some embodiments, if a change is detected (Block 702), changes in appearance are made to a user interface 70 associated with the monitoring device (Block 708).

If the system 90 of FIG. 4 determines that the subject is experiencing a certain level of stress, such as the subject having an elevated heart rate in context of low physical activity, the system 90 may increase the number of intervals and/or biometrics that are measured. For example, the system 90 may increase the number of measurement intervals or periods of the intervals in order to assess multiple biometrics, such as respiration rate, blood pressure, and RRi, for example. In this way, in response to an elevated state of subject stress, processing resources may be increased in order to initiate a more thorough biometric analysis of the subject. In contrast, when the stress level is determined to be sufficiently low, the system 90 may reduce the number of measurement intervals and/or reduce the number of biometrics being measured, such as limiting the measurement to heart rate only, for example.

Figure 18:
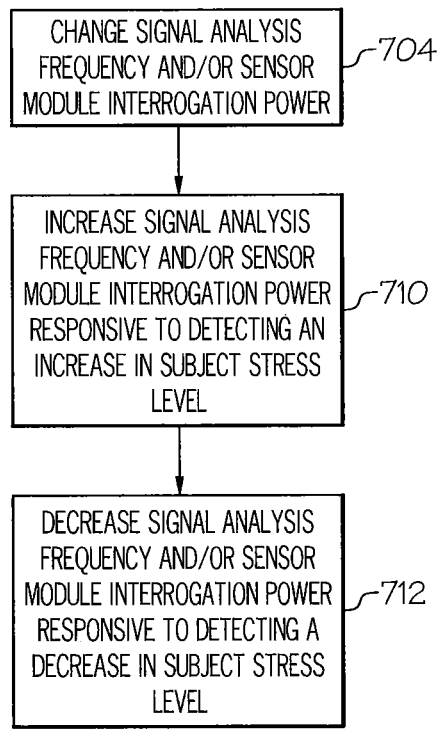

As illustrated in FIG. 18, changing signal analysis frequency and/or sensor module interrogation power (Block 704) may include increasing signal analysis frequency and/or sensor module interrogation power in response to detecting an increase in subject stress level (Block 710), and decreasing signal analysis frequency and/or sensor module interrogation power in response to detecting a decrease in subject stress level (Block 712). As a specific example, of this embodiment, the algorithm(s) 60 being executed by the processor 40 in the system 90 may be configured to operate in a "screening mode" to analyze the overall stress (well-being or health) of a subject wearing a sensor module 24, 34. When the processor determines that the stress reading is outside of an acceptable range for the subject, the processor may then focus or increase processing resource towards determining the origin of the stress condition. For example, the processor 40 may process PPG data from a sensor module 24, 34 to determine that a person is likely to have atrial fibrillation, and upon this determination the processor may increase the frequency of the pulsing of the optical emitter(s) of a PPG sensor, and/or increase the sampling rate of the PPG sensor, to collect higher acuity data for definitively diagnosing that atrial fibrillation is truly occurring.

Figure 19:
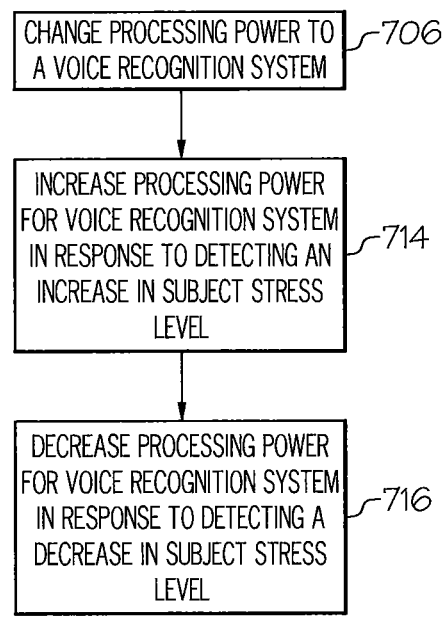

As illustrated in FIG. 19, changing processing power to a voice recognition system 84 may include increasing processing power for the voice recognition system 84 in response to detecting an increase in subject stress level (Block 714), and decreasing processing power for the voice recognition system 84 in response to detecting an decrease in subject stress level (Block 716). For example, if the system 90 of FIG. 4 determines that the subject is experiencing a certain level of stress, such as the subject having a low heart rate variability, the system 90 may increase the frequency resolution of a voice recognition system 84 such that more types of audio features can be identified, albeit at perhaps a higher power consumption expense. In contrast, when the stress level is determined to be sufficiently low, the system 90 may decrease the frequency resolution of a voice recognition system 84, such that processing power may be saved.

Figure 20:
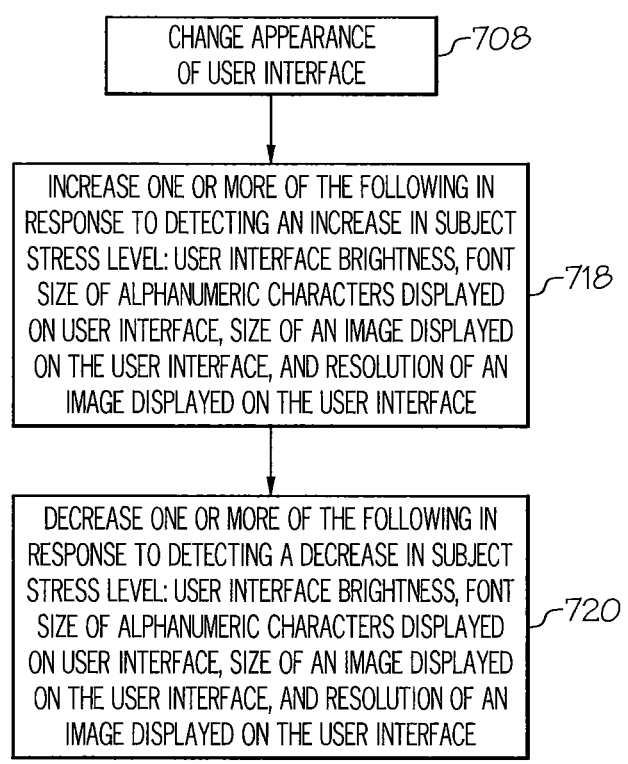

As illustrated in FIG. 20, changing the appearance of a user interface (Block 708) may include increasing user interface brightness and/or font size of alphanumeric characters displayed on the user interface in response to detecting an increase in subject stress level (Block 718), and decreasing user interface brightness and/or font size of alphanumeric characters displayed on the user interface in response to detecting an decrease in subject stress level (Block 720). For example, if the system 90 of FIG. 4 determines that the subject is experiencing a certain level of stress, such as the subject having an elevated breathing rate in context of low physical activity, the system 90 may increase the brightness of a screen and/or increase the font size of text on a mobile device, such that it is easier for the subject to interpret the screen, albeit at perhaps a higher power consumption expense. In contrast, when the stress level is determined to be sufficiently low, the system 90 may decrease the screen brightness and/or decrease the font size of text.

Example embodiments are described herein with reference to block diagrams and flowchart illustrations. It is understood that a block of the block diagrams and flowchart illustrations, and combinations of blocks in the block diagrams and flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and flowchart block or blocks, and thereby create means (functionality) and/or structure for implementing the functions/acts specified in the block diagrams and flowchart blocks.

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and flowchart blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/BlueRay).

The computer program instructions may also be loaded onto a computer and/or other programmable data processing apparatus to cause a series of operational steps to be performed on the computer and/or other programmable apparatus to produce a computer-implemented process such that the instructions which execute on the computer or other programmable apparatus provide steps for implementing the functions/acts specified in the block diagrams and flowchart blocks. Accordingly, embodiments of the present invention may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and block diagrams may be separated into multiple blocks and/or the functionality of two or more blocks of the flowcharts and block diagrams may be at least partially integrated. Finally, other blocks may be added/inserted between the blocks that are illustrated. Moreover, although some of the diagrams include arrows on communication paths to show a primary direction of communication, it is to be understood that communication may occur in the opposite direction to the depicted arrows.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A monitoring device configured to be attached to a subject, the monitoring device comprising:
   a photoplethysmography (PPG) sensor configured to measure physiological information from the subject; and
   at least one processor configured to process a photoplethysmogram produced by the PPG sensor to generate a biometric parameter in a plurality of time intervals comprising at least three time intervals, and wherein the at least one processor is configured to cause an optical emitter of the PPG sensor to have a first polling rate in a first one of the plurality of time intervals, a second polling rate in a second one of the plurality of time intervals that is lower than the first polling rate, and a third polling rate in a third one of the plurality of time intervals that is lower than the second polling rate.

2. The monitoring device of claim 1, wherein a biometric parameter in one of the plurality of time intervals is different from a biometric parameter in another one of the plurality of time intervals.

3. The monitoring device of claim 2, wherein the biometric parameter that is different comprises blood pressure.

4. The monitoring device of claim 1, wherein the first time interval occurs prior to the second time interval, and wherein the second time interval occurs prior to the third time interval.

5. The monitoring device of claim 1, wherein the monitoring device is configured to be positioned at or within an ear of the subject.

6. The monitoring device of claim 1, wherein the monitoring device is configured to be secured to an appendage of the subject.

7. A method of monitoring a subject via a monitoring device attached to the subject, wherein the monitoring device comprises a photoplethysmography (PPG) sensor and at least one processor, the method comprising:

processing, via the at least one processor, a photoplethysmogram produced by the PPG sensor to generate a biometric parameter in a plurality of time intervals comprising at least three time intervals, and wherein the at least one processor causes an optical emitter of the PPG sensor to have a first polling rate in a first one of the plurality of time intervals, a second polling rate in a second one of the plurality of time intervals that is lower than the first polling rate, and a third polling rate in a third one of the plurality of time intervals that is lower than the second polling rate.

8. The method of claim 7, wherein a biometric parameter in one of the plurality of time intervals is different from a biometric parameter in another one of the plurality of time intervals.

9. The method of claim 8, wherein the biometric parameter that is different comprises blood pressure.

10. The method of claim 7, wherein the first time interval occurs prior to the second time interval, and wherein the second time interval occurs prior to the third time interval.

11. The method of claim 7, wherein the monitoring device is configured to be positioned at or within an ear of the subject.

12. The method of claim 7, wherein the monitoring device is configured to be secured to an appendage of the subject.

13. A monitoring device configured to be attached to a subject, the monitoring device comprising:

a photoplethysmography (PPG) sensor configured to measure physiological information from the subject; and at least one processor configured to process a photoplethysmogram produced by the PPG sensor to generate a biometric parameter in a plurality of time intervals comprising at least three time intervals, and wherein each of the at least three time intervals is associated with PPG sensor data that has been sampled at a different sampling rate: a first sampling rate in a first one of the plurality of time intervals, a second sampling rate in a second one of the plurality of time intervals that is lower than the first sampling rate, and a third sampling rate in a third one of the plurality of time intervals that is lower than the second sampling rate.

14. The monitoring device of claim 13, wherein the first time interval occurs prior to the second time interval, and wherein the second time interval occurs prior to the third time interval.

15. The monitoring device of claim 13, wherein the monitoring device is configured to be positioned at or within an ear of the subject.

16. The monitoring device of claim 13, wherein the monitoring device is configured to be secured to an appendage of the subject.

17. The monitoring device of claim 13, wherein a biometric parameter in one of the plurality of time intervals is different from a biometric parameter in another one of the plurality of time intervals.

18. The monitoring device of claim 17, wherein the biometric parameter that is different comprises blood pressure.

19. A method of monitoring a subject via a monitoring device attached to the subject, wherein the monitoring device comprises a photoplethysmography (PPG) sensor and at least one processor, the method comprising:

processing, via the at least one processor, a photoplethysmogram produced by the PPG sensor to generate a biometric parameter in a plurality of time intervals comprising at least three time intervals, and wherein each of the at least three time intervals is associated with PPG sensor data that has been sampled at a different sampling rate: a first sampling rate in a first one of the plurality of time intervals, a second sampling rate in a second one of the plurality of time intervals that is lower than the first sampling rate, and a third sampling rate in a third one of the plurality of time intervals that is lower than the second sampling rate.

20. The method of claim 19, wherein the first time interval occurs prior to the second time interval, and wherein the second time interval occurs prior to the third time interval.

21. The method of claim 19, wherein the monitoring device is configured to be positioned at or within an ear of the subject.

22. The method of claim 19, wherein the monitoring device is configured to be secured to an appendage of the subject.

23. The method of claim 19, wherein a biometric parameter in one of the plurality of time intervals is different from a biometric parameter in another one of the plurality of time intervals.

24. The method of claim 23, wherein the biometric parameter that is different comprises blood pressure.

* * * * *